United States Patent [19]  [11] 4,147,865
Harnisch et al. [45] Apr. 3, 1979

[54] BENZ-(c,d)-INDOLYL COMPOUNDS

[75] Inventors: Horst Harnisch, Cologne; Alfred Brack, Odenthal, both of Fed. Rep. of Germany

[73] Assignee: Bayer Aktiengesellschaft, Leverkusen, Fed. Rep. of Germany

[21] Appl. No.: 890,688

[22] Filed: Mar. 27, 1978

Related U.S. Application Data

[63] Continuation of Ser. No. 763,142, Jan. 27, 1977, abandoned.

[30] Foreign Application Priority Data

Jan. 30, 1976 [DE] Fed. Rep. of Germany ....... 2603592

[51] Int. Cl.² ............................................ C07D 413/14
[52] U.S. Cl. .................. 544/142; 260/243.3; 260/244.4; 260/304 R; 260/306; 260/306.8 D; 260/307 D; 260/326.25; 260/326.27; 260/326.28; 260/326.29; 260/326.31; 544/121; 544/124; 544/360; 544/372; 8/1 D; 546/200; 546/272; 546/196; 546/198; 546/197; 546/187
[58] Field of Search .................. 260/326.27, 326.28, 260/293.61; 544/142, 372, 121, 124; 544/121, 124

[56] References Cited
U.S. PATENT DOCUMENTS 3,278,551 10/1966 Kleiner et al. ................. 260/326.27
3,755,353 8/1973 Baumann et al. ............... 260/326.27
3,853,911 12/1974 Schefczik ........................ 260/326.27
3,963,747 6/1976 Schefczik et al. ............... 260/326.27
4,003,898 1/1977 Gomn .............................. 260/326.27

Primary Examiner—Donald G. Daus
Assistant Examiner—Mary Lee
Attorney, Agent, or Firm—Plumley and Tyner

[57] ABSTRACT

The invention relates to compounds of the formula

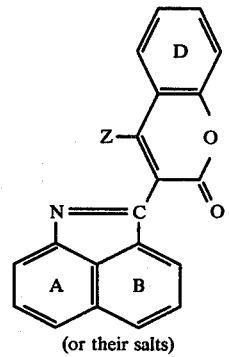

(or their salts)

wherein
Z denotes OH or $NR^1R^2$,
$R^1$ denotes hydrogen, alkyl, aralkyl, cycloalkyl or aryl,
$R^2$ denotes hydrogen or alkyl or, conjointly with $R^1$, forms an alkylene chain.

The dyestuffs are outstanding suitable for the dyeing of polyester fibres. The yellow and reddish dyeings are distinguished by good fastness to light.

3 Claims, No Drawings

BENZ-(c,d)-INDOLYL COMPOUNDS

This is a continuation of application Ser. No. 763,142 filed Jan. 27, 1977 now abandoned.

The invention relates to compounds of the general formula

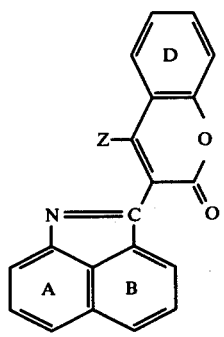

(I)

(or their salts)

wherein
Z denotes OH or $NR^1R^2$,
$R^1$ denotes hydrogen, alkyl, aralkyl, cycloalkyl or aryl,
$R^2$ denotes hydrogen or alkyl or, conjointly with $R^1$, forms an alkylene chain which is optionally interrupted by hetero-atoms,
one or two 5-membered or 6-membered carbocyclic and/or heterocyclic rings can be fused to the rings A, B and D and
the cyclic and acyclic radicals can carry substituents customary in dyestuff chemistry,
processes for their preparation, their use for dyeing high-molecular weight organic materials and materials dyed with these dyestuffs.

The fused 5-membered or 6-membered carbocyclic and/or heterocyclic rings can be partially saturated or, preferably, of aromatic character. Fused rings of this type are, formally, in each case formed by linking o-positions of the rings A, B or D with 3-membered to 4-membered divalent radicals or by linking the peri-position of A and B with 2-membered to 3-membered divalent radicals. Such divalent radicals are, in particular, saturated or unsaturated hydrocarbons which can contain 1 to 2 hetero-atoms, such as oxygen, sulphur and nitrogen, or the radical —NH—CO. When such a divalent radical, which formally forms a ring, is itself a ring or contains a ring, this ring is preferably an optionally substituted o-phenylene ring, which can contain, as particularly preferred substituents, methyl, methoxy, ethoxy, chlorine, bromine, nitro or sulpho.

Examples of such ring-forming radicals which may be mentioned are: $-CH_2-CH_2-CH_2-$, $-CH_2-CH_2-CH_2-CH_2-$, $-O-CH_2-O-CH_2-$, $-O-CH_2-CH_2-O-$, $-O-CH_2-CH_2-$, $-CH=CH-CH=CH-$, $-N=CH-CH=CH-$, $-CH=CH-C_6H_4(o)-$, $-NH-CO-$, $-O-C_6H_4(o)-$, $-NR-C_6H_4(o)-$ and $-S-C_6H_4(o)-$, the last-mentioned radicals being linked to the peri-position of A and B and the three last-mentioned radicals preferably being linked in such a way that the hetero-atom is always bonded to the ring A, and R having the meaning of H, $C_1-C_4$-alkyl, benzyl or phenyl. A $-S-C_6H_4(o)-$ radical which is linked in the indicated manner and optionally substituted in the aromatic ring by $C_1-C_4$-alkyl, $CH_3O$, $C_2H_5O$, Cl, Br, nitro or sulpho, and/or a benzo ring fused to the ring D are preferred.

Within the framework of the invention, "substituents customary in dyestuff chemistry" are understood as both non-ionic substituents and ionic substituents which promote solubility in water and amongst the ionic substituents, cationic substituents are preferred.

Examples of possible anionic radicals are sulpho and sulphinato, sulphato, disulphimide and carboxylate groups.

Suitable cationic groups are ammonium, cycloammonium or guanidinium radicals. Examples which may be mentioned are: trimethylammonium, triethylammonium, ethyldimethylammonium, benzyldimethylammonium, β-hydroxyethyldimethylammonium, N-methyl-1,2,4-triazolium-1, N-methylmorpholinium, N',N'-dimethylpiperazinium, pyridinium and 1,1-dimethylhydrazinium with customary colourless anions, such as chloride, bromide, methosulphate, p-toluenesulphonate, amidosulphonate, nitrate, bisulphate, sulphate, phosphate, acetate, lactate or chlorozincate. Cationic groups of this type can be linked direct or via a divalent intermediate member, such as $CH_2$, $CH_2-NH-CO-CH_2$, $CH_2-NH-CO-NH-CH_2$, $CO-(CH_2)_x$ in which x=1,2 or 3, $NH-CO-CH_2$, $O-CO-CH_2$, $CO-O-CH_2-CH_2$ or $SO_2-NH-(CH_2)_y$ in which y=2, 3 or 4, to an aromatic ring of the dyestuff, for example to one of the rings A, B and D or to a phenylmercapto radical.

Non-ionic substituents are particularly preferred. Examples which may be mentioned are: straight-chain or branched $C_1-C_8$-alkyl radicals, which are optionally interrupted by one to four oxygen atoms and which can contain additional substituents, such as hydroxyl.

Preferred alkyl radicals are $C_1-C_4$-alkyl radicals, which can be substituted by hydroxyl, chlorine, bromine, cyano, carboxyl, $C_1-C_4$-alkoxycarbonyl, $C_1-C_4$-alkoxycarbonyloxy, $C_1-C_4$-alkylcarbonyloxy, benzoyloxy, carbamoyl, phenoxy, phenyl-$C_1-C_3$-alkoxy, cyclohexyloxy, cyclohexyl, di-($C_1-C_4$-alkyl)-amino, acylamino, N-morpholinyl or phenyl, it being possible for the aromatic nuclei also to be substituted by radicals such as $C_1-C_4$-alkyl, $C_1-C_4$-alkoxy, chlorine, bromine, nitro or cyano. Alkyl radicals of this type are linked either direct or, advantageously, via a hetero-atom, such as oxygen, sulphur or nitrogen, to a ring system of the dyestuff molecule. The corresponding alkoxy, alkylmercapto, alkylamino or dialkylamino radicals result from linking of this type.

Further examples of suitable non-ionic substituents are: aryloxy, such as phenoxy and its derivatives substituted by chlorine, $C_1-C_4$-alkyl, amino, $C_1-C_2$-alkoxy, acetylamino, trifluoromethyl or $C_1-C_2$-alkoxycarbonyl; cyclohexyloxy; aralkoxy or aralkylmercapto, such as benzyloxy or benzylmercapto and their methyl, methoxy, nitro or chlorine derivatives; sulph-hydryl and hydroxyl; arylmercapto, such as phenylmercapto or aminophenylmercapto and their $C_1-C_4$-alkyl, trifluoromethyl, chlorine, bromine, amino, acetylamino, methylsulphonylamino, $C_1-C_2$-alkoxy or nitro derivatives, their acyclic and cyclic sulphamoyl derivatives and their sulphonic acid esters; 1-naphthylmercapto; heteryl-mercapto, such as benzthiazolylmercapto and its methyl, chlorine, $C_1-C_2$-alkoxy, nitro or acetylamino derivatives, pyridylmercapto, 4-ethylamino-6-diethylamino-1,3,5-triazol-2-yl-mercapto and 5-methylamino-1,3,4-thiadiazol-2-yl-mercapto; heteryl-$C_1-C_2$-alkylmercapto, such as 5-chloro-benzoxazol- 2-yl-methylmercapto; thiocyanato and cyano; halogen, such as fluorine, chlorine, bromine and iodine; hydrazino and amino and its derivatives which are monosubstituted or disubstituted by alkyl radicals of the abovementioned type, or by phenyl-$C_1$-$C_3$-alkyl or cyclohexyl, and/or which are monosubstituted by phenyl, wherein the phenyl radicals in each case can carry methyl, chlorine and $C_1$-$C_2$-alkoxy radicals; acylamino, such as $C_1$-$C_4$-alkyl-carbonylamino or -sulphonylamino and their chlorine derivatives, phenylcarbonylamino, phenoxycarbonylamino and phenylureido and their chlorine, methyl and $C_1$-$C_2$-alkoxy derivatives, $C_1$-$C_4$-alkoxy-carbonylamino, benzoylamino and its methyl, $C_1$-$C_4$-alkoxy, chlorine, bromine and cyano derivatives, and 1,3,5-triazinylamino radicals which carry radicals such as OH, Cl, $C_1$-$C_4$-alkoxy, phenoxy, benzyloxy, amino, $C_1$-$C_4$-alkylamino and di-($C_1$-$C_4$-alkyl)-amino in the 4-position and 6-position; examples of further non-ionic substituents are nitro, acyl radicals, especially $C_1$-$C_4$-alkanoyl and their chlorine and hydroxyl derivatives, aroyl, such as benzoyl or its chlorine, bromine, methyl, $C_1$-$C_2$-alkoxy or cyano derivatives, chlorosulphonyl, $C_1$-$C_4$-alkylsulphonyl and their chlorine and hydroxyl derivatives, vinylsulphonyl, arylsulphonyl and arylsulphinyl, such as phenylsulphonyl or phenylsulphinyl, and their methyl, chlorine, bromine, hydroxyl or $C_1$-$C_3$-alkylcarbonyloxy derivatives, aralkylsulphonyl, such as benzylsulphonyl; arylsulphonyloxy, such as phenylsulphonyloxy and its methyl, $C_1$-$C_2$-alkoxy and chlorine derivatives; carboxyl, cyano, carboxylic acid $C_1$-$C_4$-alkyl esters, benzyl esters and phenyl esters, carbamoyl or sulphamoyl and their acyclic and cyclic derivatives, such as derivatives mono- to di- ..... by $C_1$-$C_6$-alkyl or their hydroxyl, chlorine, $C_1$-$C_4$-alkoxy, cyano or di-($C_1$-$C_4$-alkyl)-amino derivatives; phenyl-$C_1$-$C_2$-alkyl, cyclohexyl, cyclohexylmethyl, phenyl and its $C_1$-$C_4$-alkyl, $C_1$-$C_4$-alkoxy, chlorine and acetamino derivatives substituted derivatives, carbo- or sulpho-pyrrolidide, carbo- or sulpho-piperidide, carbo- or sulpho-morpholide, carbo- or sulpho-piperazide and $N'$-$C_1$-$C_4$-alkyl-piperazide or -perhydroazepinide; hydrophobic alkoxysulphonyl radicals wherein the alkyl groups contain at least 4 C atoms, cycloalkoxysulphonyl, such as cyclohexyloxysulphonyl and its mono-, di- and trimethyl derivatives and phenyl-$C_1$-$C_3$-alkoxysulphonyl radicals.

Further non-ionic radicals to be mentioned are: saturated, partially saturated or quasi-aromatic 5-membered or 6-membered heterocyclic radicals which link to a ring C atom or ring N atom, including their benzo and naphtho condensation products, such as benzthiazol-2-yl, benzoxyzol-2-yl and benzimidazol-2-yl and also N-pyrrolidinyl, N-piperidinyl, N-morpholinyl, N-piperazinyl, N-imidazolyl, 1,2,3-triazol-1-yl or -2-yl, benztriazol-2-yl, naphthotriazol-2-yl, 1,2,4-triazol-1-yl, N-pyrazolyl, 4-chloropyrazolyl, 3-phenylpyrazolyl, 3-methylpyrazol-1-yl, 3-phenylpyrazolin-1-yl, N-(2-methyl)-indolinyl and N-1,2,3,4-tetrahydroquinolinyl.

Bulky radicals, such as tertiary butyl groups, are always in positions in which they do not produce stearic hindrance, that is to say in the m-position and especially in the p-position of the aromatic rings.

Acylaminoalkyl groups are, in particular, acylaminomethyl radicals. Possible acyl radicals in these groups are, for example: $C_1$-$C_4$-alkanoyl such as acetyl, chloroacetyl, $\beta$-chloropropionyl, N-morpholinoacetyl and phenoxyacetyl or phenylmercaptoacetyl radicals and their derivatives which are substituted in the phenyl nucleus by methyl, ethyl, isopropyl, tertiary butyl, methoxy, ethoxy, chlorine or acetylamino, $C_1$-$C_4$-alkanoylcarbonyl radicals, such as acryloyl and methacryloyl; phenyl-$C_1$-$C_2$-alkylcarbonyl such as phenylacetyl; aroyl, such as benzoyl, and its derivatives substituted by methyl, methoxy, chlorine, $C_1$-$C_4$-alkoxycarbonyl, cyano or carboxyl; $C_1$-$C_4$-alkylsulphonyl, such as methyl-, ethyl- or n-butyl-sulphonyl; aralkylsulphonyl, such as benzylsulphonyl; arylsulphonyl, such as phenylsulphonyl, and its derivatives substituted by methyl or chlorine, phenoxycarbonyl radicals; N-$C_1$-$C_4$-alkyl- and/or N-aryl-carbamoyl radicals, such as chloromethylaminocarbonyl and phenylaminocarbonyl and its derivatives substituted by methyl, chlorine, acetylamino, methoxy or ethoxy; 5-membered to 7-membered carboxylic acid lactams or sulphonic acid lactams which are linked to the dyestuff molecule via the lactam nitrogen, such as, for example, N-pyrrolid-2-onyl, N-piperid-2-onyl, N-perhydroazepin-2-onyl and 2-oxobenzoxazolin-3-yl, and finally cyclic diacylamides, such as N-phthalimido, N-maleimido, N-dichloromaleimido and N-dibromomaleimido, N-maleimido or N-succinimido substituted by 1 or 2 phenyl radicals, N-saccharinyl and N-succinimido. Particularly important acylaminoalkyl groups are chloroacetylaminomethyl, acryloylaminomethyl, chloromethylureidomethyl, phenylureidomethyl, benzoylaminomethyl, phenylacetylaminomethyl, phenoxyacetylaminomethyl, phenylmercaptoacetylaminomethyl and also N-pyrrolid-2-onylmethyl, N-piperid-2-onyl-methyl and N-perhydroazepin-2-onyl-methyl and, furthermore, in particular phthalimidomethyl, N-maleimidomethyl and succinimidomethyl. Alkyl radicals $R^1$ and $R^2$ preferably have 1 to 4 C atoms and can both be interrupted by 1 to 2 oxygen atoms and also carry further substituents, such as, for example, hydroxyl, $C_1$-$C_4$-alkoxy, chlorine, cyano, di-($C_1$-$C_4$-alkyl)-amino or N-morpholinyl. Preferred aralkyl radicals $R^1$ are phenyl-$C_1$-$C_2$-alkyl radicals in which the phenyl radical can also be substituted by methyl, methoxy, ethoxy, chlorine or cyano. Preferred cycloalkyl radicals $R^1$ are cyclohexyl radicals and preferred aryl radicals $R^1$ are phenyl radicals, which can also be substituted by $C_1$-$C_4$-alkyl, $C_1$-$C_2$-alkoxy or chlorine.

The following may be mentioned as suitable alkylene radicals which can be formed by $R^1$ and $R^2$ conjointly:

$$-(CH_2)_4-, \quad -(CH_2)_5-, \quad -(CH_2)_2O(CH_2)_2-,$$
$$-(CH_2)_2S(CH_2)_2-, \quad -(CH_2)_2-\underset{H}{N}-(CH_2)_2-,$$
$$-(CH_2)_2-\underset{C_1-C_4\text{-alkyl}}{N}-(CH_2)_2- \quad \text{and} \quad -(CH_2)_6-$$

$-(CH_2)_2O(CH_2)_2-$ is particularly preferred. The salts which can be formed by the compounds I are derived from known organic or inorganic colourless acids which are customarily used. Examples which may be mentioned are the acid radicals already mentioned further above and the radicals $PO_2Cl_2^{\ominus}$ and $PO_2Br_2^{\ominus}$.

Preferred radicals Z are OH groups.

Within the scope of the invention, preferred dyestuffs correspond to the formula

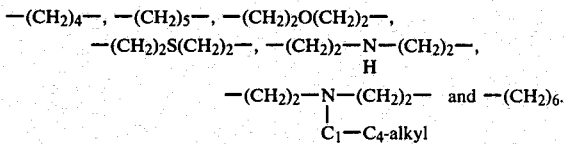

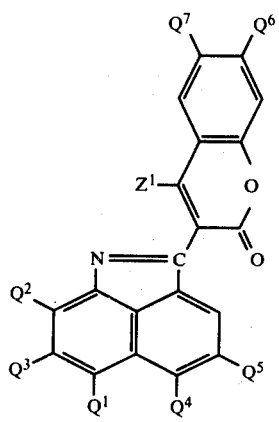

wherein $Z^1$ represents OH or $NT^1T^2$, $T^1$ represents H or a $C_1$-$C_4$-alkyl radical which is optionally substitued by $C_1$-$C_2$-alkoxy or chlorine, $T^2$ represents H or a $C_1$-$C_4$-alkyl radical which is optionally substituted by $C_1$-$C_2$-alkoxy or chlorine or, conjointly with $T^1$, represents a divalent radical of the formula —$(CH_2)_2$-T-$(CH_2)_2$—, T represents —O—, —NH—, —N(CH$_3$)—, —CH$_2$- or a direct bond, $Q^1$ represents H, fluorine, chlorine, bromine, iodine, hydroxyl, $C_1$-$C_4$-alkoxy, cyclohexyloxy, benzyloxy, phenoxy, phenylsulphonyloxy, sulphhydryl, $C_1$-$C_4$-alkylmercapto and the OH, Cl, Br, CN, $C_1$-$C_2$-alkoxy, benzyloxy and $C_1$-$C_2$-alkoxycarbonyl derivatives thereof, benzylmercapto, p-tolylmethylmercapto, phenylmercapto and its $C_1$-$C_4$-alkyl, $C_1$-$C_2$-akloxy, $CF_3$, chlorine, bromine, amino, $C_1$-$C_2$-alkylcarbonylamino, $C_1$-$C_2$-alkylsulphonylamino, chlorosulphonyl, $Q^8O$-SO—, $Q^9Q^{10}N$-SO$_2$-or nitro derivatives; naphthylmercapto, benzthiazolylmercapto and its methyl, chlorine or $C_1$-$C_2$-alkoxy derivatives; amino and its derivatives monosubstituted or disubstituted by $C_1$-$C_4$-alkyl or benzyl or monosubstituted by phenyl; $C_1$-$C_4$-alkyl-carbonylamino or -sulphonylamino and their chlorine derivatives; $C_1$-$C_4$-alkylureido or phenylureido; $C_1$-$C_2$-alkoxycarbonylamino or phenoxycarbonylamino; benzoylamino and its methyl, methoxy or chlorine derivatives; nitro; $C_1$-$C_4$-alkylsulphonyl and the chlorine and hydroxyl derivatives thereof; phenylsulphonyl or phenylsulphinyl and their $C_1$-$C_4$-alkyl, chlorine or bromine derivatives; chlorosulphonyl, $Q^8O$-SO$_2$-, $Q^9Q^{10}N$-SO$_2$-, $Q^9Q^{10}N$-CO-, $Q^{11}O$-CO- or cyano, $Q^2$ represents hydrogen, chlorine, bromine, phenylmercapto or ethyl, $Q^3$ represents hydrogen or bromine, $Q^4$ represents hydrogen, $C_1$-$C_2$-alkoxy, chlorine, bromine or phenylmercapto or represents a radical of the formula

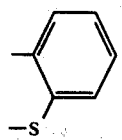

which links with the hetero-atom in position $Q^1$ and which can be substituted in the aromatic ring by methyl, methoxy, ethoxy, chlorine or bromine, $Q^5$ represents hydrogen or bromine, $Q^6$ represents hydrogen, methyl, hydroxyl, $C_1$-$C_4$-alkoxy, benzyloxy, di-($C_1$-$C_2$-alkyl)-amino, chlorine or bromine, $Q^7$ represents hydrogen, methyl, $C_1$-$C_2$-alkoxy, chlorine or bromine or, conjointly with $Q^6$, represents methylenedioxy or a radical of the formula —CH=CH-CH=CH— which is linked to position 5 of the coumarin ring system, $Q^8$ represents H, $C_4$-$C_8$-alkyl, cyclohexyl and its methyl derivatives or phenyl-$C_1$-$C_3$-alkyl, $Q^9$ represents an unsubstituted $C_1C_6$-alkyl radical, a $C_1$-$C_3$-alkyl radical which is substituted by OH, Cl, CN, $C_1$-$C_2$-alkoxy, di-($C_1$-$C_2$-alkyl)-amino, morpholino or tri-($C_1$-$C_2$-alkyl)-ammonium, or phenyl-$C_1$-$C_2$-alkyl, cyclohexyl or cyclohexylmethyl, $Q^{10}$ represents H, an unsubstituted $C_1$-$C_4$-alkyl radical or a $C_1$-$C_2$-alkyl radical which is substituted by OH, Cl, CN or $C_1$-$C_2$-alkoxy or, conjointly with $Q^9$, represents a divalent radical of the formula —$(CH_2)_2$-Q—$(CH_2)_2$- and Q represents H, $C_1$-$C_2$-alkyl, phenyl-$C_1$-$C_2$-alkyl or phenyl, and the compounds in which $Z^1=NT^1T^2$ can also be in the form of their acid salts.

In preferred compounds of the formula II, the dyestuff molecule is free from acid groups and free from additional fused heterocyclic rings.

"Bulky radicals" are preferably in those positions in which they produce no stearic hindrance.

Particularly preferred compounds are those of the formula

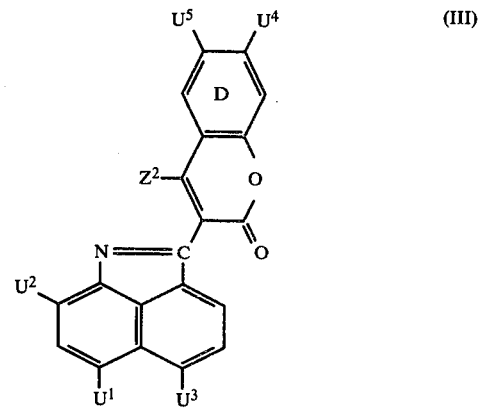

wherein $Z^2$ represents OH or $NU_6U^7$, $U^1$ represents hydrogen; chlorine, bromine or iodine; cyano or carboxylic acid C-$C_4$-alkyl ester; $C_1$-$C_4$-alkoxy or benzyloxy; phenylmercapto, which can be monosubstituted to pentasubstituted by chlorine or bromine, monosubstituted to disubstituted by $C_1$-$C_4$-alkyl or monosubstituted by $C_1$-$C_2$-alkoxy, nitro, amino, acetylamino or methylsulphonylamino; benzthiazolylmercapto, which can be substituted by methyl, $C_1$-$C_2$-alkoxy or chlorine; $C_1$-$C_4$-alkylsulphonyl, which can be substituted by OH or Cl; benzylsulphonyl; phenylsulphonyl, which can be substituted by $C_1$-$C_4$-alkyl, chlorine or bromine; or Cl-SO$_2$—, U$^8$O-SO— or U$^9$U$^{10}$N-SO$_2$—, U$^2$ represents hydrogen, chlorine, bromine, phenylmercapto or ethyl, U$^3$ represents hydrogen, C$_1$-C$_2$-alkoxy, chlorine, bromine or phenylmercapto or, conjointly with U$^1$, represents a radical of the formula

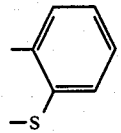

which links with the sulphur atom in positon U$^1$ and wherein the aromatic ring can contain methyl, chlorine, bromine, methoxy or ethoxy, U$^4$ represents hydrogen, methyl, C$_1$-C$_4$-alkoxy, chlorine, bromine or di-(C$_1$-C$_2$-alkyl)-amino, U$^5$ represents hydrogen, methyl, methoxy or chlorine or represents a divalent radical of the formula -CH=CH-CH=CH- which is linked to position 5 of the coumarin ring system, U$^6$ and U$^7$ each represent hydrogen or a C$_1$-C$_4$-alkyl radical which can contain methoxy or chlorine, or conjointly represent —(CH$_2$)$_4$—, —(CH$_2$)$_5$—, -(CH$_2$)$_2$O(CH$_2$)$_2$— or —(CH$_2$)$_2$-NH-(CH$_2$)$_2$—, U$^8$ represents hydrogen, C$_4$-C$_8$-alkyl, cyclohexyl or its derivatives substituted by 1-3 methyl groups, or phenyl-C$_1$-C$_2$-alkyl, U$^9$ represents an unsubstituted C$_1$-C$_6$-alkyl radical or represents β-hydroxyethyl, β-chloroethyl, β-cyanoethyl, β-C$_1$-C$_2$-alkoxyethyl, γ-di-(C$_1$-C$_2$-alkyl)aminopropyl, γ-morpholinopropyl, γ-tri-(C$_1$-C$_2$-alkyl)ammoniumpropyl, phenyl-C$_1$-C$_2$-alkyl, cyclohexyl or cyclohexylmethyl, U$^{10}$ represents hydrogen or an unsubstituted C$_1$-C$_4$-alkyl radical or represents β-hydroxyethyl, β-chloroethyl, β-cyanoethyl or β-C$_1$-C$_2$-alkoxyethyl or, conjointly with U$^9$, represents a divalent radical of the formula —(CH$_2$)$_2$-U-(CH$_2$)$_2$— and U represents —O-, -NH-, -N-(C$_1$-C$_4$-alkyl), including —N(C$_2$H$_4$OH)- or —CH$_2$-, -CH$_2$-CH$_2$- or a direct bond, and the compounds in which Z$^2$ = U$^6$U$^7$ can also be in the form of their acid salts.

Particularly valuable compounds of the formula III are those in which Z$^2$ represents OH or the N-morpholinyl radical, U$^2$, U$^3$ and U$^5$ represent hydrogen and the dyestuff molecule is free from additional fused rings. Compounds in which Z$^2$ = morpholinyl are preferably in the form of their acid salts.

Compounds of particular industrial importance are those of the formula

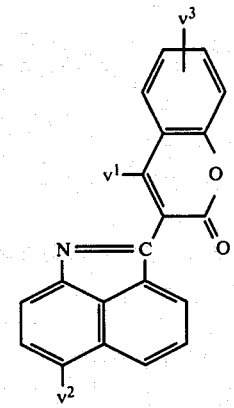

wherein

V$^1$ represents OH or the N-morpholinyl radical,

V$^2$ represents hydrogen, chlorine, bromine, iodine, phenylmercapto and its derivatives which are monosubstituted to disubstituted by chlorine, bromine or methyl or monosubstitued by tertiary butyl, methoxy, ethoxy or amino, or V$^4$-SO$_2$—, V$^3$ represents hydrogen, methyl, methoxy or chlorine, V$^4$ represents Cl, C$_1$-C$_4$-alkyl, benzyl, phenyl, methylphenyl or V$^5$V$^6$N—, V$^5$ represents C$_1$-C$_4$-alkyl, benzyl or cyclohexyl, V$^6$ represents hydrogen, C$_1$-C$_4$ -alkyl or benzyl or, conjointly with V$^5$, represents a divalent radical of the formula —(CH$_2$)$_2$-V-(CH$_2$)$_2$— and V represents —O—, -N-(C$_1$-C$_4$-alkyl)—, including —N-(CH$_2$H$_4$OH)- or —CH$_2$-, -CH$_2$-CH$_2$— or a direct bond, and the compounds in which V$^1$ = morpholinyl are in the form of their acid salts.

The dyestuffs of the formula I can be prepared by subjecting compounds of the formula

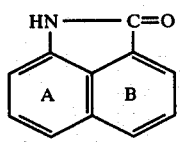

wherein

A and B have the abovementioned meaning, or derivatives thereof in which the grouping

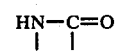

has been replaced by

HN=C—S-alkyl or HN—C(halogen)$_2$ (halogen = Cl or
  |                |
                                Br and alkyl = C$_1$—C$_3$-alkyl), to a condensation reaction with coumarin compounds of the formula

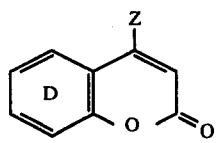

wherein

Z and D have the abovementioned meaning.

Those compounds of the formula I which correspond to the formula

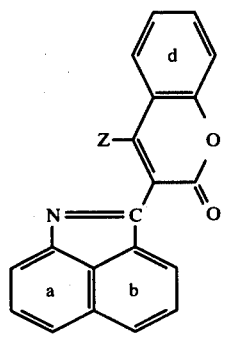

(or their acid salts)

wherein
one or two 5-membered or 6-membered carbocyclic and/or heterocylic rings can be fused to the rings a, b and d and the cyclic and acyclic radicals can carry non-ionic substituents customary in dyestuff chemistry, are preferably additionally by this process.

The condensation reaction of the compounds of the formula V with those of the formula VI is carried out in the presence of a condensing agent; if the derivatives of V which have been mentioned are used, it is possible to dispense with the presence of the condensing agent.

Suitable condensing agents are phosphorus halides, such as phosphorus pentachloride, phosphorus oxybromide and, in particular, phosphorus oxychloride.

The reactants are employed in an approximately equimolar ratio and the condensing agent which is optionally present is employed at least in a molar ratio and preferably in excess.

Appropriately, the reaction is carried out in an inert solvent or in mixtures of inert solvents. However, excess phosphorus oxyhalide can also serve as the reaction medium.

Examples of inert solvents which may be mentioned are: benzenes, such as benzene, toluene, xylene, chlorobenzene, dichlorobenzene, dichlorotoluene, nitrobenzene and benzonitrile; aliphatic hydrocarbons which are substituted by halogen, cyano and/or nitro, such as methylene chloride, chloroform, carbon tetrachloride, 1,2-dichloroethane, perchloroethylene, acetonitrile, propionitrile, nitromethane and nitropropane; and ethers, such as dioxane, tetrahydrofurane and ethylene glycol dimethyl ether or ethylene glycol diethyl ether.

When the derivative of V are reacted without a condensing agent, the solvents already mentioned are again suitable and additional solvents which may be mentioned are, for example, pyridine, glacial acetic acid, dimethylformamide, N-methylpyrrolidone, dimethylsulphoxide, sulpholane, glycol, ethylene glycol monomethyl ether and ethylene glycol monoethyl ether.

The reaction is carried out in the temperature range of about 20°–160° C. and when condensing agents are used is carried out at 20°–90° C. and preferably at 35°–75° C. When V is unsubstituted, the temperature range of 35°–55° C. is particularly preferred for this reaction. The preferred temperature range for the

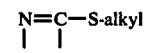

is 60°–160° C. and for HN-C(halogen)$_2$ is 90°–120° C.

A novel and industrially particularly important embodiment of the process for the preparation of dyestuffs of the formula VII is characterised in that compounds of the formula V are subjected to a condensation reaction with coumarin compounds of the formula

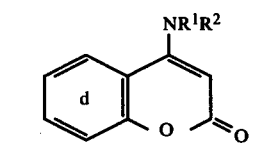

wherein
R$^1$ and R$^2$ and also d have the abovementioned meaning, in the presence of phosphorus oxychloride or phosphorus oxybromide to give dye salts of the formula

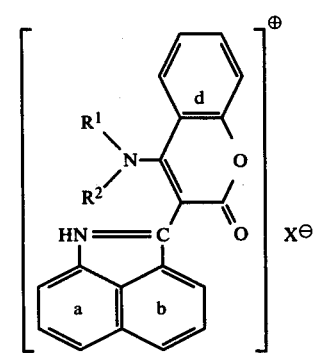

wherein
R$^1$, R$^2$, a, b and d have the abovementioned meaning and
X$^\ominus$ represents a colourless anion, and these dye salts are, if desired, saponified to give dyestuffs of the formula

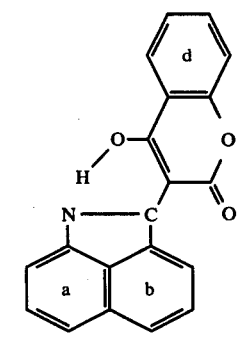

wherein
a, b and d have the abovementioned meaning.

If it is desired to isolate the dye salts IX, it is advisable, after decanting off or filtering off the solvent, to carry out an after-treatment by stirring the salts with a solvent of the type comprising the di-(lower alkyl) ketones. On such treatment, the dye salt as a rule goes temporarily into solution and then crystallises out again virtually completely, in a pure form.

If it is desired to obtain the dye bases, which are derived from IX by elimination of HX (without simultaneous saponification), the dye salts of the formula IX are treaed with customary acid acceptors, such as sodium bicarbonate, sodium carbonate, sodium acetate, potassium carbonate, dilute sodium hydroxide solution, aqueous ammonia, pyridine or triethylamine, preferably in aqueous suspension at temperatures of 10° to 70° C. and preferably 20° to 40° C. The reaction proceeds in a particularly uniform manner when the dye salt IX is dissolved in a polar, water-miscible solvent, such as dimethylformamide or N-methylpyrrolidone, and the solution is allowed to run into an aqueous solution or suspension of the acid acceptor, whilst stirring.

The saponification of the dye salts IX to give the dye-stuffs of the formula X is preferably carried out under acid conditions in aqueous solution or suspension, but preferentially in an aqueous-organic, homogeneous or two-phase, medium. Examples of suitable organic solvents are alcohols, such as methanol, ethanol, isopropanol and n-butanol, glycol, glycol monomethyl ether, glycol monoethyl ether, glacial acetic acid, acetone and those solvents which have previously been used in the condensation stage. In many cases, and especially when dye salts of the formula IX, which have been isolated as intermediates, as employed, it is advantageous to add a surface-active agent which is stable under the reaction conditions, for example a commercially available polyglycol ether with 40 to 50 ethylene oxide units (per mol). In this way, the reaction times can be greatly shortened in many cases. The amount of emulsifier added can vary within wide limits and can be about 1 to 10 percent by weight, and preferaably 3 to 8 percent by weight, relative to the dye salt IX.

The saponification is preferably carried out in the pH range of 0 to 2, and especially 0.1 to 1.0, and in the temperature range from 60° to 100° C. In order to exclude more extensive hydrolysis of X with splitting of the coumarin ring and decarboylation, the saponification time is appropriately not unnecessarily prolonged. The required saponification time is highly dependent on the conditions selected. As a rule it is from 15 minutes to 5 hours.

A particularly efficient process variant is characterised in that the intermediate isolation of the dye salts IX is dispensed with. EVen with this "one pot method", the process products of the formula X which are obtained are already so pure that further purification is as a rule not required.

The starting compounds of the formula VIII are accessible, for example, from the 4-chlorocoumarins by reaction with H-NR$^1$N$^2$. It was found that aminocoumarins VIII can be prepared more simply by reaction of 4-hydroxycoumarins of the formula

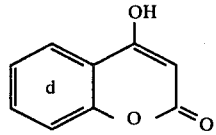

(XI)

wherein d has the abovementioned meaning, with amines of the formula H-NR$^1$R$^2$, with the elimination of water, in the temperature range of 120° to 200° C., and preferably 130° to 160° C. In many cases removal of the resulting water by distillation is to be particularly recommended. Solvents which can be used are both polar and non-polar, high-boiling solvents, such as glycol, ethylglycol, xylene, dichlorobenzene or dichlorotoluene. The reactants can be employed in a molar ratio. As a rule, an excess (5 to 15%) of amine is not troublesome.

A process for the preparation of compounds of the formula X which, industrially, is particularly valuable and economical, now consists in first subjecting hydroxycoumarins of the formula XI to a condensation reaction with amines of the formula H-NR$^1$R$^2$ in the temperature range of 120° to 200° C., to give compounds of the formula VIII, reacting these, without intermediate isolation, with compounds of the formula V and phosphorus oxychloride or phosphorus oxybromide to give dye salts of the formula IX and, if desired, saponifying these dye salts to give dyestuffs of the formula X.

Morpholine has proved particularly useful as the amine component for this "one pot process".

Compounds of the formula VII, and also those of the formula X and the dye salts of formula IX, as a rule are sufficiently stable to enable them to be subsequently sulphonated, chlorosulphonated, nitrated or halogenated and to enable the resulting substitution products to be converted into other compounds of the formula I. Electrophilic monosubstitution in the p-position relative to the ring nitrogen atom in ring a takes place particularly easily and smoothly.

In addition to the sulphonation, chlorosulphonation and nitration, halogenation reactions, such as chlorination, bromination and iodination, can also advantageously be carried out in concentrated sulphuric acid as the solvent. The starting materials and end products are readily soluble in this acid and the reaction products can be isolated without loss by discharging the reaction mixture into water.

In the case of bromination, the hydrogen bromide formed can be oxidised to bromine by sulphuric acid, so that virtually the entire amount of bromine employed is utilised for the bromination. The proportion of the sulphuric acid which acts as the oxidising agent is reduced to sulphurous acid (some SO$_2$ escapes).

However, as is known, the oxidation potential is adequate for the oxidation of hydrogen bromide only when the sulphuric acid is sufficiently concentrated. As a rule, the sulphuric acid must be of at least 96% strength for this purpose. Reoxidation of the hydrogen bromide can also be effected by other oxidising agents, such as, for example, chlorine or sulphuryl chloride.

Thus, a further subject of the invention is a process for the preparation of compounds of the formula

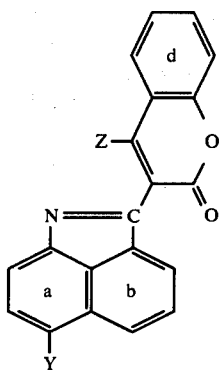

wherein
Y represents a chlorine, bromine or iodine atom and
Z, a, b and d have the meaning indicated above (in formula VII), characterised in that compounds of the formula

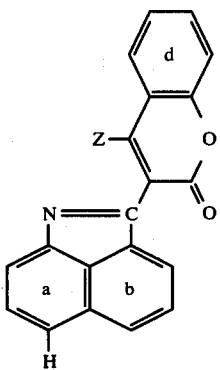

wherein
Z, a, b and d have the abovementioned meaning, are reacted in 96 to 100% strength sulphuric acid and in a temperature range of 0° to 100° C., preferably 15° to 80° C., with metal-free nuclear-halogenating agents.

Preferred metal-free nuclear-halogenating agents are chlorine, sulphuryl chloride, bromine and ICl. The nuclear-halogenating agent is advantageously employed in an amount greater than the equivalent amount, say in a 2 to 20%, and preferably 3 to 10%, excess; in the case of chlorine, sulphuryl chloride and ICl, the equivalent amount is to be understood as a molar ratio of 1:1 and in the case of $Br_2$, the equivalent amount is to be understood as half the molar amount (per mol of XVI).

Under the indicated conditions, the danger of multiple halogenation is usually slight, even when a relatively large excess of the said nuclear-halogenating agents is used.

The replacement of halogen and especially bromine, by mercapto radicals takes place considerably more easily and more smoothly than the reaction described for halogeno-naptholactams in German Offenlegungsschrift (German Published Specification) No. 2,233,937.

A further subject of the invention is a process for the preparation of mercapto compounds of the formula

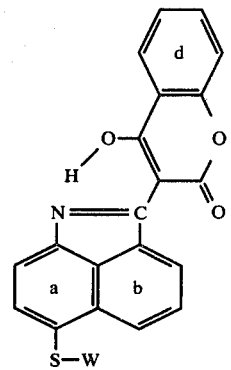

wherein
W represents hydrogen, alkyl, aralkyl, cycloalkyl, aryl or a heterocyclic radical, which radicals can contain further non-ionic substituents, and
a, b and d have the meaning mentioned above (in formula VII), characterised in that compounds of the formula XII are reacted with compounds of the formula WSH and an inorganic or organic base. An organic solvent which is dipolar and aprotic or polar and protic, but free from groups which have an acid reaction in water, is preferably used.

Alkyl radicals W are, for example, $C_1$-$C_8$-alkyl radicals, especially $C_1$-$C_5$-alkyl radicals, which can also carry further substituents, such as OH, Cl, Br, CN, $C_1$-$C_4$-alkoxy, $C_1$-$C_4$-alkoxycarbonyloxy, $C_1$-$C_4$-alkylcarbonyloxy, benzoxyloxy, carboxyl and $C_1$-$C_4$-alkoxycarbonyl.

Preferred aralkyl radicals W are phenyl-$C_1$-$C_2$-alkyl radicals, which can be substituted in the phenyl nucleus, for example by methyl, methoxy, nitro or chlorine.

Preferred cycloalkyl radicals are cyclohexyl groups. Preferred aryl radicals W are phenyl or naphthyl radicals which can contain further substituents, such as $C_1$-$C_4$-alkyl, $C_1$-$C_2$-alkoxy, trifluoromethyl, chlorine, bromine, amino, $C_1$-$C_4$-alkylcarbonylamino, $C_1$-$C_4$-alkylsulphonylamino, nitro, phenyl or $Q^9Q^{10}N$-$SO_2$—, in which $Q^9$ and $Q^{10}$ have the meaning indicated above (in formula II).

The reaction is carried out in the temperature range from 50° to 120° C. and when compounds of the formula XII in which R = $NR^1R^2.HX$ are used is preferably carried out at 55° to 70° C. and in the case where R = OH is preferably carried out at 85° to 110° C.

Bases which can be used are customary hydroxides, carbonates, alcoholates or acetates of alkali metals or of ammonia, such as sodium hydroxide, potassium hydroxide, sodium carbonate, potassium carbonate, ammonium hydroxide, sodium methylate or potassium acetate, or organic bases, especially tertiary bases, such as pyridine or triethylamine, and also anion exchange resins.

The components XII, WSH and the base are employed in an approximately molar ratio. However, when R = $NR^1R^2.HX$, a further equivalent of the base is required in order to blind HX.

The presence of water can be troublesome during the reaction, since partial hydrolysis of the coumarin ring and decarboxylation can occur at the same time. It is therefore particularly preferred to carry out the reaction under virtually anhydrous conditions. If the base is employed as an aqueous solution, it is advisable first substantially to distil off the water together with a little solvent in vacuo at temperatures which are still markedly below the reaction temperatures. In many cases the reaction proceeds particularly rapidly and uniformly when XII is previously pre-treated with the base under anhydrous conditions in the solvent for about 20 to 90 minutes, and preferably 1 hour, at the reaction temperature subsequently chosen.

Preferred protic solvents are ethylene glycol $C_1$-$C_4$-alkyl ethers and diethylene glycol $C_1$-$C_4$-alkyl ethers, and preferred dipolar aprotic solvents are dimethylformamide, N-methylpyrrolidone or hexamethylphosphoric acid triamide.

The compounds of the formula I are fluorescent dyestuffs of high tinctorial strength in the range of yellow to blue colour shades and are suitable for dyeing and printing, and for bulk dyeing, natural, semi-synthetic and synthetic high-molecular weight organic materials.

Whilst the preferred field of application for the acid representatives of these compounds is in dyeing wool, silk, paper and synthetic polyamides and the cationic quaternary salts are especially suitable for dyeing polymers which contain polyacrylonitrile, and also acid-modified polyester and polyamide fibres as well as paper, the emphasis for the use of the neutral, water-insoluble dyestuffs lies in dyeing and printing hydrophobic textile fibre or fabric materials, such as acetate rayon, triacetate and, in particular, polyesters, preferably polycondensates of terephthalic acid and ethylene glycol. Because of their good heat stability, compounds of the formula X are also suitable for bulk dyeing, especially for bulk dyeing polyester materials.

The dyestuffs are distinguished by high clarity and brilliance of the colour shade and generally by a high affinity and good build-up capacity and good fastness properties in use and dyestuffs of the formula III in particular have a very high degree of fastness to light. The fluorescent dyestuffs known hitherto do not possess these advantageous properties to the same extent.

Dye salts of the formula IX, and especially those in which $NR^1R^2$ represents morpholinyl and the rings a and b are unsubstituted and free from additional fused rings, have the striking characteristic that, whilst they are readily soluble in water, they are already taken up under normal dyeing conditions in the form of the water-insoluble, neutral compound of the formula X, which is especially fast to light, on polyester, acid-modified polyester, triacetate and acetate fibres. The water-soluble dye salts IX hydrolyse in the dyebath at the rate at which they are taken up as the neutral substance X. The advantage over the neutral disperse dyestuffs X is that it is possible to dispense with expensive auxiliaries which are a load on the effluent and also that the saponification stage (IX → X) is saved during their preparation.

Accordingly, a new process for dyeing textile materials made of polyester, acid-modified polyester, triacetate or acetate rayon with dyestuffs of the formula X is characterized in that water-soluble dye salts of the formula IX are used in an aqueous or water-containing dyebath. Dyeing is carried out under the normal conditions of the exhaustion process, from a long liquor, with or without a carrier, under normal pressure (100° C.) or under the autogenous pressure (130° C.). Sublimable dyestuffs of the formula I which are free from groups conferring solubility in water, and especially those dyestuffs of the formula X which are free from additional fused rings and in total are substituted only by $C_1$-$C_2$-alkyl or -alkoxy, chlorine or $C_1$-$C_4$-alkylsulphonyl, are outstandingly suitable for printing polyester, acid-modified polyester, triacetate or acetate rayon by the transfer printing process. Transfer of the dyestuff from suitable temporary supports, such as paper or metal foils, to the fabric to be printed is effected at about 160° to 240° C., and preferably 200° to 220° C., for 30 to 60 seconds.

Very fast dyeings on the abovementioned substrates are also obtained with compounds of the formula

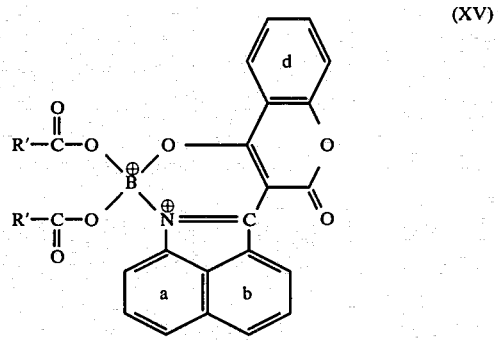

wherein
R′ represents alkyl, cycloalkyl, aralkyl or aryl, but preferably represents $C_1$-$C_4$-alkyl, $CF_3$ or phenyl and a, b and d have the meaning mentioned above (in formula X).

The dyestuffs XV are prepared by subjecting compounds of the formula X to a condensation reaction with boric acid and an aliphatic, cycloaliphatic or aromatic acid anhydride or acid halide, preferably a $C_1$-$C_4$-alkanoyl anhydride, trifluoroacetic anhydride or benzoic anhydride, at elevated temperature. The reaction is carried out in the temperature range of 80° to 170° C., preferably of 90° to 160° C., in an inert organic solvent, such as sulpholane, and in preferred cases in a boiling carboxylic acid anhydride.

As a rule, the substances of the formula XV are dyestuffs which have a high melting point and can be recrystallised without decomposition from solvents such as dimethylformamide. In dilute organic solution they display a fluorescence stronger than that of the particular starting dyestuffs of the formula X. They are suitable not only as fibre dyestuffs but also as fluorescent marking and storage identification dyestuffs.

EXAMPLE 1a 78 g of phosphorus oxychloride are added to 50.2 g of 4-hydroxycoumarin and 50.8 g of naphthostyril in 150 g of 1,2-dichloroethane and the mixture is stirred for 10 hours at 40° C. A clear red solution first forms; the reaction product crystallises out from this in the form of red crystals. 170 ml of ethylene glycol monoethyl ether and 330 ml of water are added, whilst cooling slightly, and 99 g of 45% strength sodium hydroxide solution are added dropwise at such a rate that the temperature rises to 50° C. but does not exceed this temperature. The mixture is stirred for a further 2 hours at 50° C. and cooled to room temperature and the mixture is stirred for a further 5 hours. The crystalline precipitate is filtered off, washed with 200 ml of isopropanol and then with 1 liter of water and dried in vacuo at 80° C. 56 g of the compound of the formula

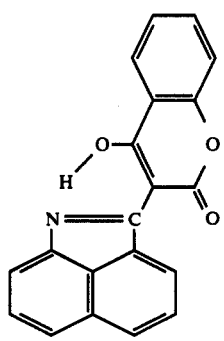

are obtained. The dyestuff can be purified by recrystallisation from dimethylformamide.

EXAMPLE 1b 55.5 g of phosphorus oxychloride are added to 50.2 g of 4-hydroxycoumarin and 50.8 g of naphthostyril in 200 g of ethylene glycol dimethyl ether and the mixture is stirred for 8 hours at 45° C. After cooling to room temperature, the crystalline precipitate is filtered off, washed with about 30 ml of ethylene glycol dimethyl ether, pressed off well and dissolved in about 120 ml of dimethylformamide, whilst warming slightly, and this solution is then added dropwise to a solution of 100 g of sodium bicarbonate in 1 liter of water and the mixture is stirred. The dyestuff of the formula (1), which is obtained as crystals, is filtered off, washed thoroughly with water and dried at 80° C. Yield: 44 g. For purification, the dyestuff can be recrystallised from dimethylformamide.

EXAMPLE 1c 62 g of 2-methylmercapto-benz-[c,d]-indole hydromethosulphate and 33 g of 4-hydroxycoumarin in 500 ml of dimethylformamide, with the addition of 20 g of pyridine, are heated to the boil, under reflux and whilst stirring, for 15 minutes and then cooled. The crystalline precipitate is filtered off, washed with ethanol and dried in vacuo at 60° C. 37 g of product are obtained and by concentrating the mother liquor, stirring the residue with ethanol and isolating and drying the product, a further 21 g of the compound of the formula (1) are obtained as a yellow-red crystalline powder. A 0.25% strength dyeing on polyester fibres (exhaustion process, 100° C.) gives a brilliant, slightly reddish-tinged yellow shade with good fastness properties, and especially good fastness to light. The compound gives a brilliant yellow transfer print (45″, 210° C.) on polyester fabric. The dyestuffs which follow are prepared in an analogous manner from the corresponding starting materials: Compounds of the formula

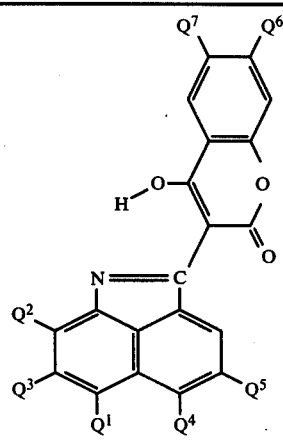

| Example No. | $Q^1$ | $Q^2$ | $Q^3$ | $Q^4$ | $Q^5$ | $Q^6$ | $Q^7$ | Colour shade on polyester (130° C.) |
|---|---|---|---|---|---|---|---|---|
| (2) | H | H | H | H | H | $OCH_3$ | H | reddish-tinged yellow |
| (3) | Br | H | H | H | H | $OC_2H_5$ | H | orange |
| (4) | Cl | H | H | H | H | $OC_4H_9$-(n) | H | orange |
| (5) | H | $C_2H_5$ | H | $OC_2H_5$ | H | $OCH_2C_6H_5$ | H | yellowish-tinged red |
| (6) | $OC_6H_{11}$ | H | H | H | H | $(OC_2H_4)_2OCH_3$ | H | red-orange |
| (7) | $SO_2CH_3$ | H | H | H | H | H | $CH_3$ | reddish-tinged yellow |
| (8) | $OCH_3$ | H | H | H | H | H | Cl | yellowish-tinged red |
| (9) | $OC_4H_9(n)$ | H | H | H | H | $N(CH_3)_2$ | H | red |
| (10) | H | H | H | $OCH_3$ | H | $N(C_2H_5)_2$ | H | red |
| (11) | Br | H | H | Br | H | H | H | orange |
| (12) | Cl | H | H | Cl | H | $CH_3$ | H | yellow-orange |
| (13) | Br | Br | H | H | H | H | H | orange |
| (14) | Cl | Cl | H | H | H | H | $CH_3$ | orange |
| (15) | Br | H | Br | Br | Br | H | H | orange |
| (16) | $OCH_2C_6H_5$ | H | H | H | H | H | $OCH_3$ | yellowish-tinged red |
| (17) | $OC_6H_5$ | H | H | H | H | H | H | red-orange |
| (18) | —N—$C_6H_5$<br>\|<br>$CH_3$ | H | H | H | H | H | Br | violet |
| (19) | —$SC_6H_5$ | H | H | H | H | H | $OCH_3$ | scarlet |
| (20) | —$SCH_3$ | H | H | H | H | —O—$CH_2$—O— | | red |
| (21) | CN | H | H | H | H | H | H | yellow |
| (22) | $COOC_2H_5$ | H | H | H | H | H | $CH_3$ | yellow |
| (23) | $COOC_4H_9$-(n) | H | H | H | H | H | H | yellow |
| (24) | $COOC_6H_5$ | H | H | H | H | H | H | yellow |
| (25) | $COOCH_2$—$C_6H_6$ | H | H | H | H | H | H | yellow |

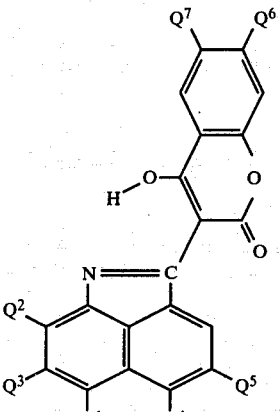

| Example No. | Q¹ | Q² | Q³ | Q⁴ | Q⁵ | Q⁶ | Q⁷ | Colour shade on polyester (130° C.) |
|---|---|---|---|---|---|---|---|---|
| (26) | COOH | H | H | H | H | H | H | yellow |
| (27) | CON($C_2H_5$)$_2$ | H | H | H | H | H | H | yellow |
| (28) | F | H | H | H | H | H | $OC_2H_5$ | reddish-tinged yellow |
| (29) | CO—N⟨ ⟩ (pyrrolidine) | H | H | H | H | H | H | yellow |
| (30) | OH | H | H | H | H | H | OH | red-orange |
| (31) | O—$SO_2$—cyclohexyl | H | H | H | H | H | H | orange | as well as the compound of the formula

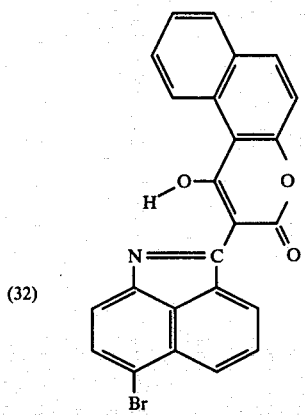

(32)    orange

If, in Example 1, the 2-methylmercapto compound is replaced by an equivalent amount of 2-ethylmercapto-benz-[c,d]-indole hydroethosulphate or 2-n-propylmercapto-benz-[c,d]-indole hydroiodide, compound (1) is obtained in similar yields.

EXAMPLE 33

92 g of phosphorus pentasulphide are introduced in the course of 40 minutes into 500 ml of pyridine at 20° to 60° C., whilst stirring and cooling slightly, and the mixture is then stirred for a further 1 hour at 50° to 60° C. 110 g of 4-amino-benzo-[k,l]-thioxanthenyl-3-carboxylic acid lactam, the preparation of which is described in Example 68 of German Offenlegungsschrift (German Published Specification) Pat. No. 2,233,937, are introduced into the resulting suspension, the mixture is warmed to 50° to 55° C. for 6 hours and to 65 to 70° C. for 2 hours and discharged into 3 liters of cold water and the suspension is stirred for 1 hour. The crystalline precipitate is filtered off, washed with water and dried in vacuo at 50° C. 93 g of the corresponding thiolactam are obtained. 44 ml of dimethyl sulphate are added dropwise to 88 g of this compound in 1.2 liters of chloroform at 50° C., whilst stirring, and the mixture is stirred at 55° C. for 10 hours. The solvent is then stripped off in vacuo (waterbath) and the residue is stirred with 1 liter of acetone. The crystalline precipitate is filtered off, washed with acetone and dried in vacuo at 50° C. 106 g of the corresponding methylmercapto hydromethosulphate are obtained.

42 g of this hydromethosulphate, 16.5 g of 4-hydroxycoumarin and 10 g of pyridine in 350 ml of dimethylformamide are heated to the boil, under reflux and whilst stirring, for 30 minutes and then cooled. The crystalline precipitate is filtered off, washed with ethanol, recrystallised from dimethylformamide, washed with ethanol and dried in vacuo at 60° C. 28 g of the compound of the formula

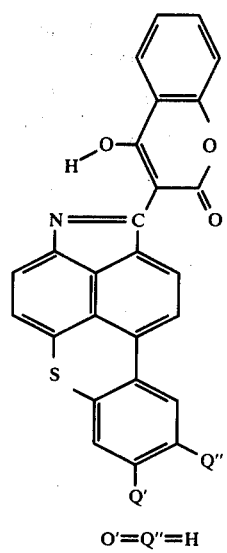

(33)

Q'=Q"=H are obtained.

A dyeing on polyester (130° C.) displays a brilliant violet colour shade with good fastness properties.

The compounds which follow and are listed in the table were prepared by the same method:

| Example No. | Q' | Q" | Colour shade (polyester, 130° C.) |
|---|---|---|---|
| (34) | $CH_3$ | H | violet |
| (35) | $OCH_3$ | H | violet |
| (36) | $OC_2H_5$ | H | violet |
| (37) | H | Cl | violet |
| (38) | H | Br | violet |

EXAMPLE 39

23 g of 2,2-dichloro-benz-[c,d]-indoline (prepared according to the instructions in Example 1a of German Offenlegungsschrift (German Published Specification) No. 1,445,624) are suspended in 250 ml of anhydrous chlorobenzene, 16.2 g of 4-hydroxycoumarin are added and the mixture is warmed to 100° C. for 15 minutes, whilst stirring, during which hydrogen chloride escapes. 10 g of bleaching earth (Tonsil) are added, the hot suspension, which is at 100° C., is filtered through a fluted filter, the filtrate is again clarified with 8 g of bleaching earth, the filtrate is evaporated in vacuo (waterbath) and the residue is dried in vacuo at 70° C. 19.5 g of the compound of the formula (1) are obtained.

The compounds of the formula (2) to (38) can also be prepared by the same method.

If 2,2-dichloro-benz-[c,d]-indoline is replaced by an equivalent amount of 2,2-dibromo-benz-[c,d]-indoline, which is prepared in an analogous manner using $PBr_5$ in place of $PCl_5$, compound (1) is obtained in a similar yield.

EXAMPLE 40

92 g of phosphorus oxychloride are added to 64.4 g of 4-aminocoumarin and 60.8 g of benz-[c,d]-indolin-2-one in 300 ml of anhydrous xylene and 300 ml of anhydrous 1,2-dichloroethane, whilst stirring, and the mixture is stirred at 65° C. for 4 hours and then cooled to room temperature. The solvent mixture is decanted off and the residue is warmed with 400 ml of acetone to 45° C. and this mixture is cooled to 20° C. The crystalline precipitate is filtered off, washed with acetone until the filtrate is clear and dried in vacuo at 50° C. 88 g of the dye salt of the formula

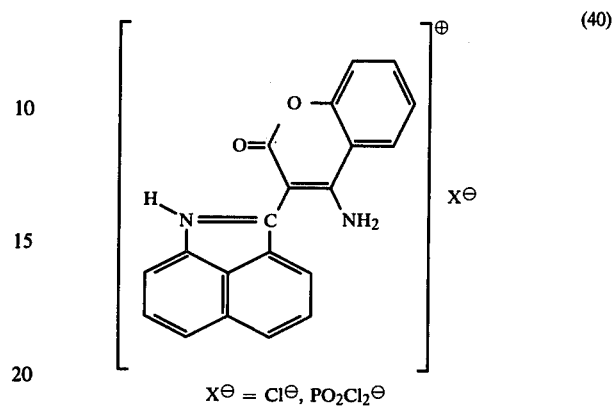

$X^\ominus = Cl^\ominus, PO_2Cl_2^\ominus$ are obtained in the form of dark red crystals.

80 g of dye salt (40) are stirred in 1 liter of dimethylformamide for 15 minutes at room temperature. The resulting suspension is introduced in small portions into a solution of 100 g of sodium bicarbonate in 1 liter of water, whilst stirring (pH 7 to 8) and the mixture is stirred for 15 hours at room temperature. The crystalline precipitate is filtered off, washed with water and dried in vacuo at 50° C. 45 g of the compound of the formula

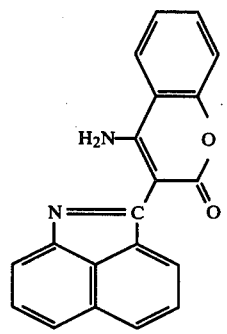

(41)

are obtained in the form of brown-yellow crystals.

4-Aminocoumarin was prepared in the following way:

97.2 g of 4-hydroxycoumarin and 69.3 g of ammonium acetate in 300 ml of ethylene glycol are heated to 70° C. for 3 hours, whilst stirring, and to 160° C. for 6 hours, the mixture is cooled to 60° C., 1 liter of water is added, whilst stirring, and the mixture is cooled to room temperature. The colourless crystalline precipitate is filtered off, washed with water and dried in vacuo at 60° C. 96 g of 4-aminocoumarin in an almost pure form are obtained The dye salts of the formula

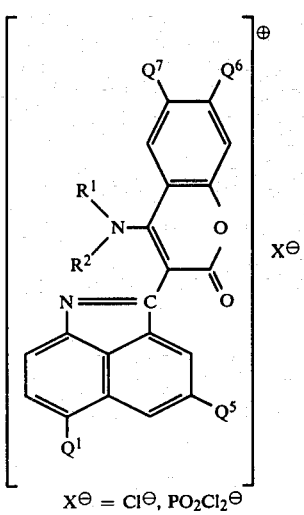

$X^\ominus = Cl^\ominus, PO_2Cl_2^\ominus$ which are listed in the table which follows were prepared from the corresponding starting materials by the same method:

| Example | R¹ | R² | Q¹ | Q⁵ | Q⁶ | Q⁷ |
|---|---|---|---|---|---|---|
| (42) | CH₂ | CH₂ | H | H | H | H |
| (43) | C₂H₅ | C₂H₅ | Cl | H | H | H |
| (44) | N'-Methyl-N-piperazinyl | | H | H | H | H |
| (45) | n-C₄H₉ | H | H | H | CH₃ | |
| (46) | C₂H₄Cl | C₂H₄Cl | H | H | H | CH₃ |
| (47) | C₂H₄OCH₃ | CH₃ | H | OCH₃ | H | H |
| (48) | C₂H₄OC₂H₅ | C₂H₄OC₂H₅ | H | H | H | H |
| (49) | N-Pyrrolidinyl | | Br | H | CH₃O | H |
| (50) | N-Piperidinyl | | H | H | H | H |
| (51) | N-Merpholinyl | | —S—C₆H₅ | H | H | H |
| (52) | N-Piperazinyl | | H | H | H | CH₃O |

EXAMPLE 53

10 g of 4-hydroxycoumarin are introduced into a solution of 92 g of morpholine in 600 ml of xylene, whilst stirring, and the mixture is stirred for 30 minutes. A further 157 g of 4-hydroxycoumarin are added to the crystal suspension which has formed and the mixture is stirred for a further 4 hours at room temperature and then for 5.5 hours under reflux under a water separator. 500 ml of 1,2-dichloroethane are added, 100 ml of solvent are distilled off, 229.5 g of phosphorus oxychloride are added at 50° C. and 145g of benz-[c,d]-2-one are added in portions in the course of 15 minutes at 50° to 55° C., the mixture is warmed to 55° C. for 7 hours and cooled to 40° C., the solvent phase is decanted off from the oily lower phase, 800 ml of acetone are added to the oily residue and the mixture is stirred for 30 minutes at 40° C. and for 3 hours at 15° C. The crystalline dye salt is filtered off, washed with acetone until the filtrate is clear and dried in vacuo at 50° C. 275 g of the dye salt of the formula

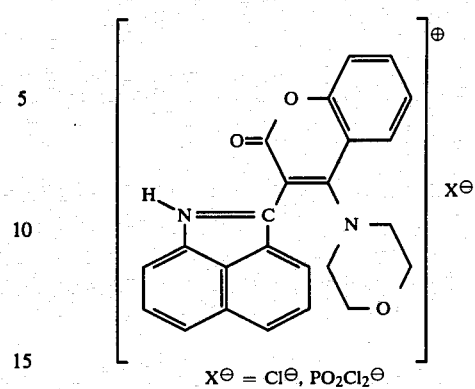

(53)

$X^\ominus = Cl^\ominus, PO_2Cl_2^\ominus$ are obtained in the form of luminous red crystals.

The dye salt gives a red-orange dyeing on polyacrylonitrile fibres. A 0.25% strength dyeing on modified polyester fibres (Dacron 64(R)) or an unmodified polyester fibres consisting of polyethylene terephthalate gives a brilliant, deep, somewhat reddish-tinged yellow, fluorescent dyeing with good fastness properties and in particular good fastness to light. The properties of the dyeing are identical to those of a dyeing obtained with the disperse dyestuff of the formula (1) prepared according to the instructions of Example 1.

Dye salts which have very similar dyeing properties are obtained when equivalent amounts of 4-hydroxy-6-methylcoumarin, 4-hydroxy-7-methylcoumarin, 4-hydroxy-6-chlorocoumarin, 4-hydroxy-6-methoxycoumarin or 4-hydroxy-7-ethoxycoumarin are employed in place of 4-hydroxycoumarin.

EXAMPLE 54

46.2 g of 4-morpholinocoumarin (prepared according to the instructions of Example 53, with intermediate isolation), 28.4 g of phosphorus pentoxide, 46 g of phosphorus oxychloride and 49.6 g of 6-bromo-benz-[c,d]-indolin-2-one are successively introduced into a mixture of 120 ml of anhydrous xylene and 140 ml of ahydrous 1,2-dichloroethane. The reaction mixture is heated to 85° C. for 5 hours, whilst stirring, and then cooled to room temperature. The solvent is decanted off, 450 ml of acetone are added to the residue and the mixture is warmed to 50° C. and cooled to room temperature. The crystalline precipitate is filtered off, washed with 250 ml of acetone and dried in vacuo at 50° C. 72 g of the dye salt of the formula

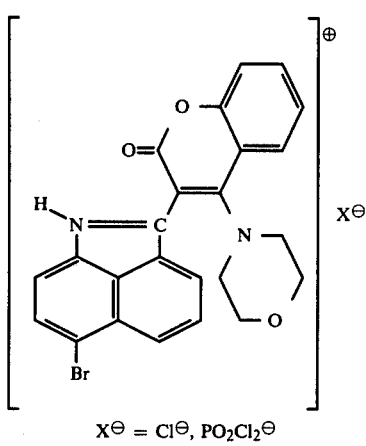

(54)

$X^\ominus = Cl^\ominus, PO_2Cl_2^\ominus$ are obtained in the form of dark red crystals which are soluble in water.

EXAMPLE 55

30 g of the dye salt of the formula (53) in a mixture of 60 ml of xylene, 70 ml of 1,2-dichloroethane, 70 ml of ethylene glycol monoethyl ether, 95 ml of water and 10.5 g of concentrated hydrochloric acid are heated, in the presence of 1.5 g of $^{(R)}$Avolan IW, to 70° to 73° C. for 2.5 hours. After cooling, the crystalline precipitate is filtered off, washed with isopropanol and then with water and dried in vacuo at 70° C. 15.5 g of the compound of the formula (1) are obtained in a pure form.

A similar result is obtained when the dye salt is heated to the boil for 15 minutes in a mixture (5:1) of glacial acetic acid and concentrated hydrochloric acid, the reaction mixture is discharged into water and the dyestuff is isolated and dried.

EXAMPLE 56

92 g of morpholine in 600 ml of xylene are reacted with 167 g of hydroxycoumarin, as described in Example 53, 800 ml of 1,2-dichloroethane are added, 100 ml of solvent are distilled off, 229.5 g of phosphorus oxychloride are added at 50° C. and 145 g of benz-[c,d]-indolin-2-one are added in the course of 15 minutes at 50° to 55° C., the mixture is warmed to 53° to 55° C. for 7 hours, whereupon the dye salt of the formula (53) precipitates in the form of liminous red crystals, 700 ml of ethylene glycol monoethyl ether are added at 50° C. and 960 ml of water and 290 g of 45% strength sodium hydroxide solution are then added, whilst cooling, and the mixture is warmed to 70° to 73° C. for 2 hours, whilst stirring, cooled to 20° C. and stirred for 3 hours at this temperature. The crystalline precipitate is filtered off, washed first with a total of 750 ml of isopropanol and then with about 3 liters of water, pressed off well and dried in vacuo at 70° C. 184 g of the compound of the formula (1) are obtained in a very pure form as a golden yellow crystalline powder. If the reaction is carried out for 13 hours at 40° C., 193.5 g of the compound (1) are obtained.

Similar results are obtained when equivalent amounts of 4-hydroxy-6-methylcoumarin, 4-hydroxy-7-methylcoumarin or 4-hydroxy-6-chlorocoumarin are employed in place of 4-hydroxycoumarin or when the 6-chloro, 6-bromo, 6-methoxy, 6-methylmercapto, 6-methylsulphonyl, 5-methoxy or 4-methoxy derivative of benz-[c,d]-indolin-2-one is employed at condensation temperatures of 75° to 85° C. in place of benz-[c,d]-indolin-2-one.

Compound (1) is obtained in a similar yield when 2,2-dichloro-benz-[c,d]-indoline is employed, in the above instructions, in place of phosphorus oxychloride and benz-[c,d]-indolin-2-one and in an amount equivalent to the last-mentioned compound and the resulting mixture is warmed to 100° C. for 30 minutes and the subsequent procedure is the same as indicated in the instructions.

EXAMPLE 57

156.5 g of the compound of the formula (1) are introduced, in portions, at 20° to 25° C., in the course of 30 minutes into 750 ml of 100% strength sulphuric acid (D = 1.85), whilst stirring and with slight external cooling, the mixture is stirred for 1 hour, 3 g of iodine are added, 36 g of bromine are added dropwise below the surface of the solution in the course of 30 minutes at 20° to 25° C., with slight external cooling, the mixture is stirred for 1 hour at 20° to 25° C., for 4 hours at 40° C., for 2 hours at 40° to 60° C. and for 2 hours at 60° C., a further 9 g of bromine are added dropwise below the surface of the solution, the mixture is stirred for a further 5 hours at 60° C., 390 ml of water are added dropwise, starting at 40° C., at such a rate that the temperature rises to 95° C. and the mixture is stirred for a further 2 hours at 95° C. the crystalline precipitate is filtered off, washed in several portions with a total of 25 liters of water at 70° C. until neutral, pressed off well and, if desired, dried at 70° C. 192 g of the compound of the formula

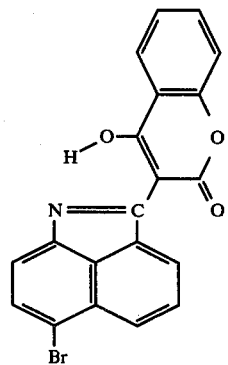

(57)

are obtained as an orange coloured crystalline powder. A 0.35% strength dyeing on polyester fabric under high temperature conditions (130° C. in a closed vessel) gives a brilliant, yellowish-tinged orange colour shade with good fastness properties and in particular good fastness to light. The The dyestuff of the formula (57) is obtained in the same yield and quality when the following procedure is employed:

210 g of the water-moist compound of the formula (1), which has a solids content of 74.8% (corresponding to a dry weight of 156.5 g) and was obtained in accordance with the instructions of Example 56 but without drying the product, are introduced, in portions, in the course of 30 minutes at 20° to 25° C. into 400 ml of 100% strength sulphuric acid (D = 1.85), whilst stirring and with slight external cooling, the mixture is stirred for 1 hour at 20° to 25° C. and cooled to 5° C., 376 g of oleum (with 20% excess $SO_3$) are added dropwise at 5° to 10° C. in the course of 30 minutes, with external cooling and whilst stirring, the temperature is allowed to rise to 20° C., 3 g of iodine are added and the bromination is carried out in accordance with the above instructions. For working up, the mixture, which has been cooled to room temperature, is discharged into 7.5 l of water pre-warmed to 60° C. and the temperature is allowed to rise to 95° C. The product is isolated as indicated above.

EXAMPLE 58

12.5 g of the compound of the formula (1) are introduced, at 20° to 25° C., into 60 ml of concentrated sulphuric acid (D = 1.84), whilst stirring, the mixture is stirred for 30 minutes, 5.5 g of sulphuryl chloride are added dropwise in the course of 30 minutes, the mixture is warmed to 60° C. in the course of 3 hours, whilst stirring, and is stirred for 3 hours at 60° C. and then discharged into 600 ml of water pre-warmed to 60° C. and the mixture is stirred for a further 20 minutes. The crystalline precipitate is filtered off, washed with hot water until neutral and dried at 60° C. 12.2 g of the compound of the formula

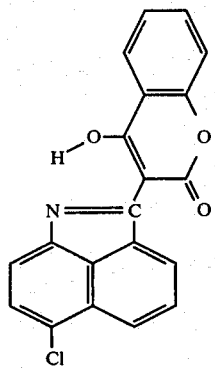

(58)

are obtained as a yellow-orange coloured crystalline powder, the degree of purity of which is already adequate for most coloristic requirements. A particularly high degree of purity can be achieved by subsequent recrystallisation from chlorobenzene, the solution being clarified by filtration using bleaching earth (Tonsil).

An approximately 0.4% strength dyeing on polyester fibres gives a brilliant, deep reddish-tinged yellow shade with good fastness properties and in particular good fastness to light.

EXAMPLE 59

32.8 g of finely powdered iodine are suspended in 40 ml of glacial acetic acid and the suspension is treated at 20° to 30° C. with dry chlorine gas until iodine trichloride begins to separate out as orange coloured crystals from the clear dark solution which is first formed. Iodine is then added gradually, whilst continuing to stir, until the iodine trichloride has just gone completely into solution again. For example, 18 g of iodine were required for this purpose. The ICl solution thus prepared is added dropwise, at 20° to 25° C., to a solution of 80 g of the compound of the formula (1) in 800 ml of 94% strength sulphuric acid (D = 1.84), whilst stirring, the mixture is stirred for 4 hours at 40° C., for 1 hour at 40° to 60° C. and for 5 hours at 60° C. and is cooled to room temperature, the reaction solution is discharged into 6 liters of water prewarmed to 60° C. and the temperature is allowed to rise to 70° to 80° C. and then to fall to 40° C. The crystalline precipitate is filtered off, washed in several portions with a total of 20 liters of water at 70° C. until neutral, pressed off well and, if desired, dried in vacuo at 70° C. 106 g of the compound of the formula

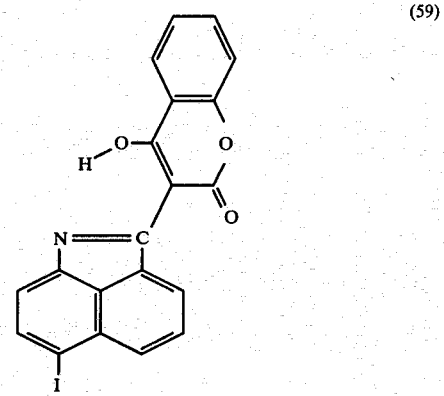

(59)

are obtained as an orange coloured crystalline powder. A dyeing on polyester fibres under high temperature conditions (130° C. in a closed vessel) gives a brilliant orange colour shade with good fastness properties and in particular good fastness to light.

EXAMPLE 60

117 g of the dye salt of the formula (53) are introduced, at 20° to 25° C., into 220 ml of 100% strength sulphuric acid (D = 1.85), whilst stirring and cooling. As soon as a clear solution has formed, 0.75 g of iodine is added, 26 g of bromine are added dropwise in the course of 30 minutes at 20° to 25° C., the mixture is stirred for a further 16 hours at room temperaure, the solution is discharged onto 500 g of ice, the mixture is stirred for 1 hour and the crystalline precipitate is filtered off, stirred with 400 ml of isopropanol, filtered off again and dried in vacuo at 40° C. 124 g of a dye salt are obtained; the cation of the salt is identical to that described in formula (54) and the anion of the salt consists mainly of $HSO_4^-$.

EXAMPLE 61

125 g of the compound of the formula (1) are introduced into 800 ml of concentrated sulphuric acid (D = 1.84) at 20° to 25° C., the mixture is stirred for 30 minutes, a mixture of 22 ml of concentrated nitric acid (D = 1.51) and 100 ml of concentrated sulphuric acid is then added dropwise, whilst stirring, and the mixture is stirred for 15 hours at room temperature and discharged into 8 liters of water at 60° C., whereupon the temperature is allowed to rise to 70° to 80° C. and then to cool to 40° C. The crystalline precipitate is filtered off, washed with 20 liters of water until neutral and, if desired, dried in vacuo at 50° C. 136 g of the compound of the formula

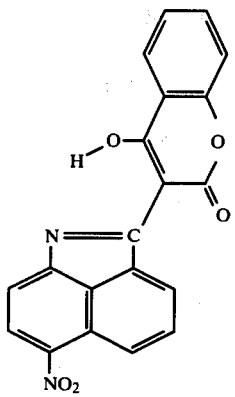

(61)

are obtained as an orange coloured crystalline powder. A 0.4% strength high temperature dyeing (130° C.) on polyester fabric gives a brilliant orange colour shade with good fastness properties.

EXAMPLE 62

156.5 g of the compound of the formula (1) are introduced into 450 g of chlorosulphonic acid at 40° C., whilst cooling and stirring, the reaction mixture is stirred for 30 minutes at 80° C. and discharged onto 2.5 kg of ice, whilst stirring, and the mixture is stirred for 5 minutes. The crystalline precipitate is filtered off, washed with water and suspended in 400 ml of ice-cold ethanol and the product is filtered off and dried in vacuo at 25° C. 190 g of the compound of the formula

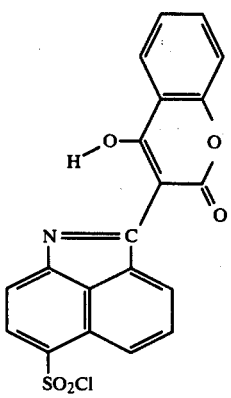

(62)

are obtained as an orange coloured crystalline powder.

EXAMPLE 63

50 g of the compound of the formula (1) are introduced into 500 g of oleum, which contains 10% of free $SO_3$, at 10° to 15° C., whilst cooling and stirring, and the reaction mixture is stirred for 16 hours at 20° to 25° C., and discharged onto 3 kg of ice. The crystalline precipitate is filtered off, washed with 2% strength sodium chloride solution and dried in vacuo at 70° C. 56 g of the dye acid of the formula

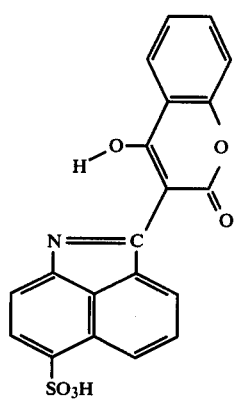

(63)

are obtained as a yellow crystalline powder. A 0.4% strength dyeing on polyamide fabric (Perlon) gives a very clear, reddish-tinged yellow shade with good fastness properties.

EXAMPLE 64

526 g of the water-moist compound of the formula (61), corresponding to a dry weight of 78.6 g, are introduced into 2,500 ml of water at 50° C., 50 ml of sodium bisulphide solution (18 to 20% by volume of free $H_2S$) are added dropwise at 40° to 45° C. and the mixture is stirred for 6 hours at 42° to 45° C. The crystalline precipitate is filtered off, washed with water and dried in vacuo at 50° C. 72 g of the compound of the formula

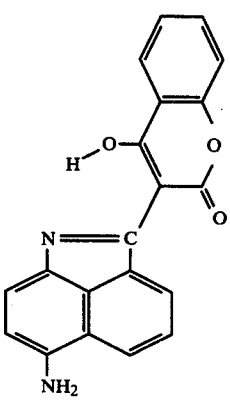

(64)

are obtained in the form of dark blue crystals.

EXAMPLE 65

6.6 g of 4-hydroxy-3-[6'-amino-benz-[c,d]-indol-2'-yl]-coumarin (compound 64) are dissolved in 80 ml of N-methyl-pyrrolidone by warming. The solution is cooled to 40° C., 2.3 g of chloroacetyl chloride are added at this temperature, with slight external cooling, and the mixture is stirred for 1 hour at 40° C. and discharged into 400 ml of water. The crystalline precipitate is filtered off, washed with water and dried in vacuo at 60° C. 7.9 g of the compound of the formula (65)

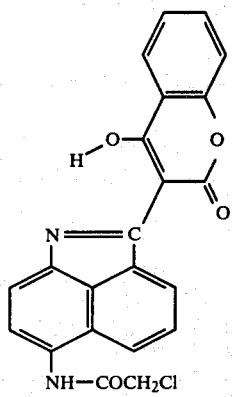

are obtained. On polyester fibres it displays a brilliant red colour shade with good fastness properties.

If the chloroacetyl chloride is replaced by 2.9 g of benzoyl chloride, 3.5 g of the compound of the formula (66)

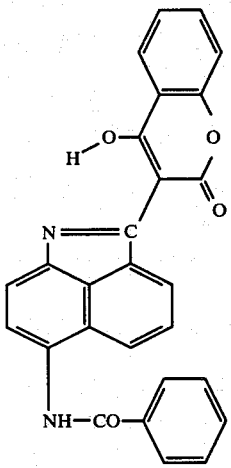

are obtained in an analogous manner.

This compound also displays a brilliant red colour shade, which has good fastness properties, on polyester fibres.

Dyestuffs which have similar properties on polyester fibres are obtained when an equivalent amount of one of the following acylating agents is employed in place of chloroacetyl chloride: methanesulphonyl chloride, 2-chloroethanesulphonyl chloride, 4-chlorobutanesulphonyl chloride, 3-chloropropionyl chloride, acetic anhydride, 4-chlorobutyryl chloride, isovaleryl chloride, dimethylcarbamic acid chloride, dimethylsulphamic acid chloride, ethyl isocyanate, propyl isocyanate, isopropyl isocyanate, isobutyl isocyanate, tert.-butyl isocyanate, phenyl isocyanate, chlorobenzoyl chloride, toluyl chloride, 4-methoxybenzoyl chloride, chloroformic acid ethyl ester or chloroformic acid phenyl ester.

EXAMPLE 67

6.6 g of the compound of the formula (64) are dissolved in 80 ml of N-methylpyrrolidone by warming. The solution is cooled to 40° C., 4 g of calcium carbonate and 5.5 g of benzyl chloride are added, the mixture is warmed to 130° C. for 5 hours and filtered hot, the filtrate is discharged into 300 ml of ice water and the mixture is stirred for 10 minutes. The crystalline precipitate is filtered off and dried in vacuo at 50° C. 9.3 g of the compound of the formula (67)

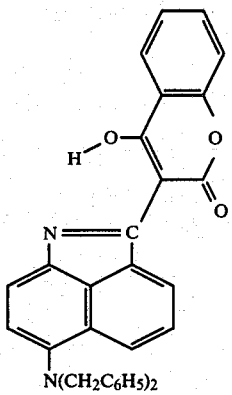

are obtained. The dyestuff can be purified by recrystallisation from glacial acetic acid. It dyes polyester fibres in a reddish-tinged blue colour shade.

If the benzyl chloride is replaced by an equivalent amount (8.5 g) of 1-bromobutane, the dyestuff of the formula (68)

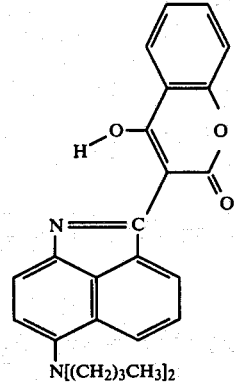

is obtained after 8 hours .. 125° C. It also dyes polyester fibres in a reddish-tinged blue colour shade.

EXAMPLE 69

83 g of the compound of the formula 63, in the form of the sodium salt, are suspended in 400 ml of dimethylformamide, 32 g of dimethyl sulphate are added, the reaction mixture is stirred for 5 hours at 80° C. and discharged into 1 l of water and the mixture is stirred for 30 minutes. The crystalline precipitate is filtered off, washed with water and dried in vacuo at 50° C. 76 g of the corresponding sulphonic acid methyl ester are obtained. 41 g of this ester are suspended in 180 ml of cyclohexyl bromide, 0.5 g of tributylhexadecylammonium bromide is added and the mixture is heated to the boil for 4 hours, whilst distilling off the methyl bromide formed, and cooled to room temperature. The crystalline precipitate is filtered off, washed with a little ethanol and dried in vacuo at 50° C. 41 g of the compound of the formula (69)

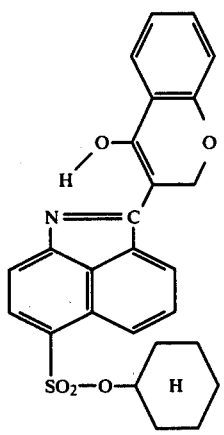

are obtained as a golden yellow crystalline powder. A 0.3% strength dyeing on polyester fabrics (exhaustion process, 100° C.) gives a very clear, somewhat reddish-tinged yellow shade with good fastness properties.

The dyestuffs of the formula given below, which are listed in the table which follows and coloristically are similarly valuable, are prepared by the same method.

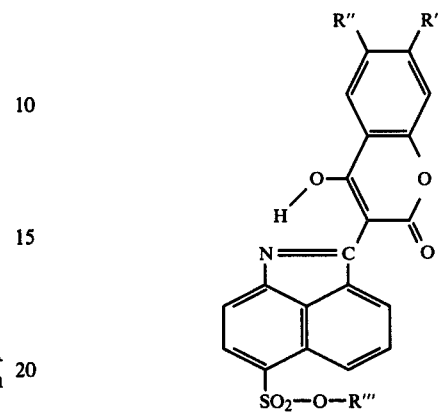

| Example | R''' | R' | R'' | Colour shade on polyester (100° C.) |
|---|---|---|---|---|
| (70) | $(CH_3)_2CH-CH_2-$ | $CH_3$ | H | brilliant reddish-tinged yellow |
| (71) | $(CH_3)_2CH-CH_2-CH_2-$ | H | $CH_3$ | brilliant reddish-tinged yellow |
| (72) | $CH_3-CH(CH_3)-CH_2-CH(CH_3)-$ | H | H | brilliant reddish-tinged yellow |
| (73) | 4-methylcyclohexyl (mixture of isomers) | H | H | brilliant reddish-tinged yellow |
| (74) | Isooctyl— | $OCH_3$ | H | brilliant reddish-tinged yellow |
| (75) | cyclohexyl | H | Cl | brilliant reddish-tinged yellow |
| (76) | 3,3,5-trimethylcyclohexyl | H | H | brilliant reddish-tinged yellow |
| (77) | cyclohexylmethyl— | H | H | brilliant reddish-tinged yellow |
| (78) | 1-phenylethyl— | H | H | brilliant reddish-tinged yellow |
| (79) | 3-phenylpropyl— | H | H | brilliant reddish-tinged yellow |

-continued

| Example | R''' | R' | R'' | Colour shade on polyester (100° C.) |
|---|---|---|---|---|
| (80) | -CH2-C6H5 | H | H | brilliant reddish-tinged yellow |
| (81) | -CH2-CH2-C6H5 | OC2H5 | H | brilliant deep reddish-tinged yellow |
| (82) | tetrahydronaphthyl | H | H | brilliant reddish-tinged yellow |

EXAMPLE 83

41.2 g of the compound of the formula (62), 12.8 g of piperidine and 86.6 g of sodium carbonate are introduced into a mixture of 670 ml of water and 200 g of ethanol, the reaction mixture is heated to the boil for 2 hours under reflux, whilst stirring, and discharged hot into 4.5 liters of water at 60° C. and the mixture is stirred for 15 minutes. The crystalline precipitate is filtered off, washed with water, recrystallised from 520 ml of dimethylformamide, washed with ethanol and dried in vacuo at 60° C. 32 g of the compound of the formula

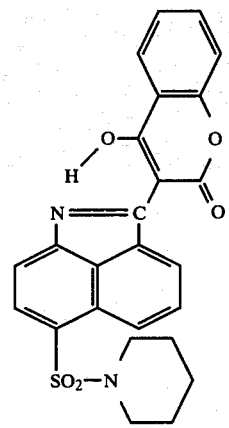

(83)

are obtained as a yellow crystalline powder. A 0.36% strength dyeing on polyester fabric by the high temperature process (130° C., closed vessel) gives a brilliant, somewhat reddish-tinged yellow shade with good fastness properties, such as good fastness to light and sublimation.

The following compounds of the formula

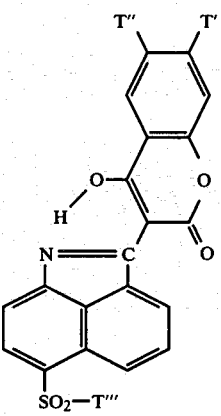

which are listed in the table, are prepared by the same method.

| Example | T''' | T' | T'' | Colour shade on polyester (130° C., high temperature dyeing) |
|---|---|---|---|---|
| (84) | -N(pyrrolidinyl) | H | CH3 | brilliant, somewhat reddish-tinged yellow |
| (85) | -N(morpholinyl) | H | OCH3 | brilliant, reddish-tinged yellow |
| (86) | -N(hexahydroazepinyl) | CH3 | H | brilliant, reddish-tinged yellow |
| (87) | -N(N'-methylpiperazinyl) | H | H | brilliant, somewhat reddish-tinged yellow |

-continued

| Example | T''' | T' | T'' | Colour shade on polyester (130° C., high temperature dyeing) |
|---|---|---|---|---|
| (88) | −N(piperazine)N−CH₂−CH₂OH | H | H | brilliant, somewhat reddish-tinged yellow |
| (89) | −NH−CH₂−CH₂−CH₂−N(CH₃)₂ | H | H | brilliant, somewhat reddish-tinged yellow |
| (90) | −N((CH₂)₃CH₃)₂ | H | CH₃ | brilliant, somewhat reddish-tinged yellow |
| (91) | −N(piperazine)NH | H | H | brilliant, somewhat reddish-tinged yellow |
| (92) | −N(CH₃)₂ | CH₃ | H | brilliant, reddish-tinged yellow |
| (93) | −N(CH₂−CH₂Cl)₂ | Cl | H | brilliant, somewhat reddish-tinged yellow |
| (94) | −N(CH₂−CH₂OH)₂ | H | H | brilliant, somewhat reddish-tinged yellow |
| (95) | −N(piperazine)N−(CH₂)₃CH₃ | H | H | brilliant, somewhat reddish-tinged yellow |
| (96) | −N(CH₂−CH₂−O−CH₃)₂ | H | H | brilliant, somewhat reddish-tinged yellow |
| (97) | −N(−(CH₂)₅CH₃)(C₂H₅) | H | H | brilliant, somewhat reddish-tinged yellow |
| (98) | −N(CH₃)−CH₂−CH₂−CH₂−N(morpholine)O | H | H | brilliant, somewhat reddish-tinged yellow |
| (99) | −N(CH₂−cyclohexyl)₂ | H | CH₃ | brilliant, somewhat reddish-tinged yellow |
| (100) | −NH−cyclohexyl(H) | H | CH₃ | brilliant, somewhat reddish-tinged yellow |
| (101) | −NH₂−CH₂−cyclohexyl(H) | H | H | brilliant, somewhat reddish-tinged yellow |
| (102) | −N(CH₂−CH₂−CN)₂ | H | H | brilliant, somewhat reddish-tinged yellow |
| (103) | −N(CH₃)−CH₂−CH₂−phenyl | H | H | brilliant, somewhat reddish-tinged yellow |

EXAMPLE 104

14.4 g of the compound of the formula (89) are introduced into a mixture of 300 ml of anhydrous chlorobenzene and 30 ml of anhydrous 1,2-dichloroethane, 3.6 ml of dimethyl sulphate are added at 70° C. and the mixture is stirred for 3 hours at 70° C. and cooled to room temperature. The crystalline precipitate is filtered off, washed with toluene, recrystallised from 1.2 liters of ethylene glycol monomethyl ether, washed with a little ethanol and dried in vacuo at 60° C. 12 g of the compound of the formula

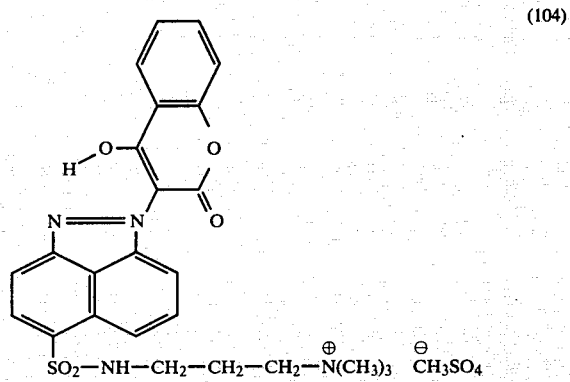

(104)

$SO_2-NH-CH_2-CH_2-CH_2-\overset{\oplus}{N}(CH_3)_3 \quad \overset{\ominus}{C}H_3SO_4$ are obtained as a yellow crystalline powder. A 0.4% strength dyeing on polyacrylonitrile fibres gives a brilliant, somewhat reddish-tinged, fluorescent yellow shade with good fastness properties.

Compounds (87) and (88) can also be converted into valuable cationic dyestuffs in an analogous manner.

EXAMPLE 105

41.2 g of the compound of the formula (62) are introduced, at 5° C., into a freshly prepared solution of 51 g of crystallised sodium sulphite in 100 ml of water, whilst stirring. The pH is adjusted to a constant value of 8 to 10 by adding sodium hydroxide solution dropwise and during this addition the temperature is allowed to rise to 35° C. The mixture is stirred for a further 16 hours at room temperature. The crystalline precipitate is filtered off and dried in vacuo at 40° C. 34 g of the compound of the formula

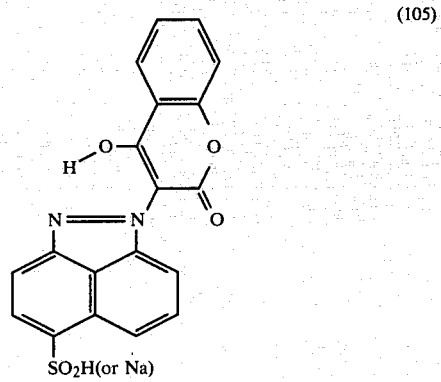

(105)

$SO_2H$(or Na)

are obtained.

The sulphinate of the formula (105) gives a brilliant yellow dyeing on polyamide fibres. It is an important intermediate product for the preparation of alkylsulphonyl and aralkylsulphonyl compounds, which can be obtained from the sulphinate by reaction with alkyl halides or aralkyl halides according to known methods.

EXAMPLE 106

196 g of the compound of the formula (57) in 3.9 liters of ethylene glycol monoethyl ether are heated to the boil for 1 hour under reflux, and whilst stirring, the mixture is cooled to 105° C., 75 g of anhydrous potassium carbonate are added, the mixture is warmed to 100° C. for 1 hour, 60 g of thiophenol are added, the mixture is warmed to 100° C. for 10 minutes and cooled to 25° C., 60 g of glacial acetic acid are added dropwise and the mixture is stirred for 15 minutes. The crystalline precipitate is filtered off, washed with 300 ml of ethanol, washed in several portions with a total of 1.5 liters of water, pressed off well and dried in vacuo at 70° C. 193 g of the compound of the formula

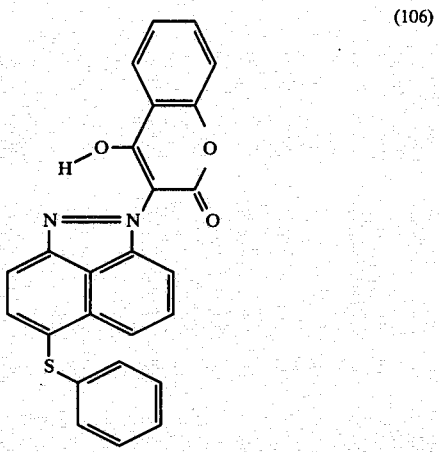

(106)

are obtained as a dark red crystalline powder. A 0.3% strength dyeing on polyester fabric (130° C., closed vessel) gives a brilliant, luminous yellowish-tinged red colour shade which has good fastness properties and in particular good fastness to light.

EXAMPLE 106a 196 g of the compound of the formula (57) in 620 ml of dimethylformamide are warmed to 100° C. for 30 minutes, 75 g of anhydrous potassium carbonate to 60.3 g of thiophenol are added successively and the mixture is stirred for a further 30 minutes at 100° C. The reaction mixture is allowed to cool, whilst stirring, and is stirred for a further 10 hours. The crystalline precipitate is filtered off, washed with 50 ml of dimethylformamide and then with 1.5 liters of water, pressed off well and dried in vacuo at 70° C. 194 g of the compound of the formula (106) are obtained.

Dyestuffs of similarly high quality, which are listed in the table which follows, are prepared by the same method.

The dyestuffs correspond to the formula

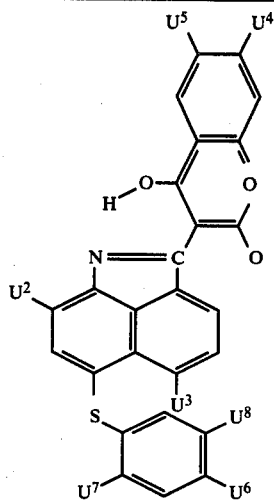

| Example | U² | U³ | U⁴ | U⁵ | U⁶ | U⁷ | U⁸ | Colour shade (polyester, 130° C.) |
|---|---|---|---|---|---|---|---|---|
| (107) | H | H | H | H | CH₃ | H | H | red |
| (108) | H | H | H | CH₃ | C(CH₃)₃ | H | H | red |
| (109) | H | H | H | H | Cl | H | H | yellowish-tinged red |
| (110) | H | H | H | H | Br | Br | H | yellowish-tinged red |
| (111) | H | H | H | H | H | H | H | red |
| (112) | H | Br | H | H | CF₃ | H | H | red |
| (113) | H | S—C₆H₅ | H | H | H | H | H | bluish-tinged red |
| (114) | Br | H | H | H | Br | H | H | red |
| (115) | Cl | H | H | H | H | CH₃ | CH₃ | bluish-tinged red |
| (116) | H | H | H | H | H | NH₂ | H | bluish-tinged red |
| (117) | H | H | H | H | H | NH₂ | OCH₃ | deep bluish-tinged red |
| (118) | H | H | H | H | H | NH₂ | CH₃ | bluish-tinged red |
| (119) | H | H | OC₂H₅ | H | H | NH₂ | OC₂H₅ | deep bluish-tinged red |
| (120) | H | H | OCH₃ | H | Cl | Cl | Cl | bluish-tinged red |
| (121) | H | H | H | H | OCH₃ | H | H | scarlet |
| (122) | H | H | H | H | NO₂ | H | H | deep yellowish-tinged red |
| (123) | H | H | H | Cl | CH₃CONH | H | H | bluish-tinged red |
| (124) | H | H | H | H | CH₃SO₂NH | H | H | bluish-tinged red |
| (125) | H | H | H | CH₃ | H | Cl | Cl | yellowish-tinged red |
| (126) | H | H | H | H | H | Cl | Cl | yellowish-tinged red |
| (127) | H | H | H | H | H | NH—COCH₃ | H | bluish-tinged red |

In Example 111 the 6,8-dibromo compound is reacted with twice the amount of thiophenol and in Example 113 the 3,4-dibromo compound is reacted with twice the amount of thiophenol. Further analogous examples correspond to the formula

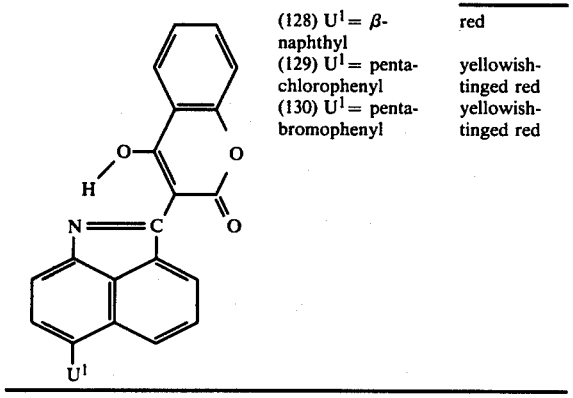

| | Colour shade |
|---|---|
| (128) U¹ = β-naphthyl | red |
| (129) U¹ = pentachlorophenyl | yellowish-tinged red |
| (130) U¹ = pentabromophenyl | yellowish-tinged red |

The thiophenols and the thionaphthol employed are readily accessible according to the instructions in German Offenlegungsschrift (German Published Specification) No. 2,116,978.

EXAMPLE 131

36 g of the compound of the formula (57) in 600 ml of ethylene glycol monoethyl ether are heated to the boil for 30 minutes, under reflux and whilst stirring, the mixture is cooled to 50° C. and, at this temperature, a solution of 21.2 g of 2-mercaptobenzthiazole in 160 ml of ethylene glycol monoethyl ether and 11.2 g of 45% strength sodium hydroxide solution are added. 100 ml of water-containing solvent are then distilled off in vacuo at 50° C., the mixture is heated to the boil for 10 hours, under reflux and whilst stirring, and cooled to room temperature, 42 g of glacial acetic acid ate added and the crystal suspension is stirred for a further 15 minutes. The crystalline precipitate is filtered off, washed with ethanol until the filtrate is clear and then washed with water and dried in vacuo at 70° C. 39 g of the compound of the formula (131)

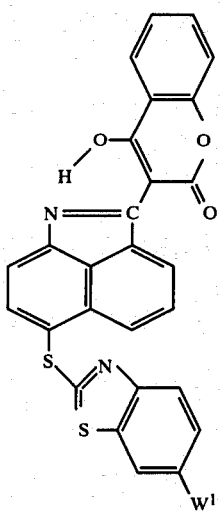

W¹ = H are obtained as a red crystalline powder. Pad-thermosol dyeing on polyester fabric (fixing for 30' at 210° C.) gives a brilliant red-orange colour shade with good fastness properties.

The dyestuffs listed in the table which follows are prepared by the same method. They give dyeings on polyester which are of similar quality to those obtained with (131).

| Example | W¹ | Dyeing on polyester (30 'at 210 ° C.) |
|---------|-----|---------------------------------------|
| (132)   | CH₂ | red-orange |
| (133)   | Cl  | red-orange |
| (134)   | OCH₃ | scarlet |
| (135)   | OC₂H₅ | scarlet |

EXAMPLE 136

The procedure is as indicated in Example 131 but the solution of 21.2 g of 2-mercaptobenzthiazole in ethylene glycol monoethyl ether and sodium hydroxide solution is replaced by a solution of 18.8 of 2-mercapto-5-methylamino-1,3,4-thiadiazole in 170 ml of ethylene glycol ethyl ether and 12 g of 45% strength sodium hydroxide solution. 38 g of the compound of the formula (136)

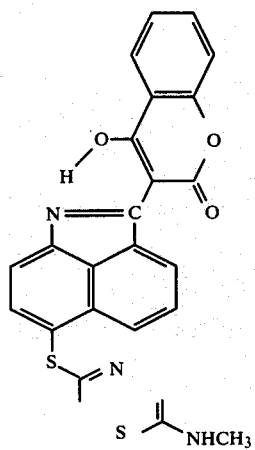

are obtained.

EXAMPLE 137

30 g of the compound of the formula (57) in 500 ml of ethylene glycol monoethyl ether are heated to the boil for 1 hour, under reflux and whilst stirring, the mixture is cooled to 105° C., 13 g of anhydrous potassium carbonate are added, the mixture is warmed to 100° C. for 1 hour, 9 g of thioglycollic acid methyl ester and 6 ml of pyridine are added, the mixture is warmed to 110° C. for 30 minutes and cooled to 20° C., 45 g of glacial acetic are added dropwise, the mixture is stirred for 15 minutes and the product is washed with water, suspended in 250 ml of ethanol, filtered off and washed with ethanol. For further purification, the product is twice extracted by boiling with chloroform and filtered hot. The filtrate is evaporated to dryness in vacuo on a waterbath. 24 g of the compound of the formula (137)

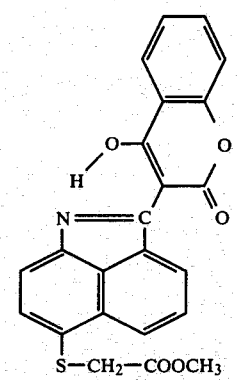

are obtained as a dark red crystalline powder. A dyeing on polyester fibres (exhaustion process at 100° C.) gives a luminous yellowish-tinged red colour shade.

The dyestuff of the formula

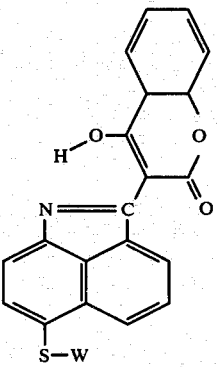

which are listed in the table which follows are by the same method.

| Ex. | W | Colour shade (polyester, 100° C.) |
|-----|---|-----------------------------------|
| (138) | —CH₂—CH₂OH | bluish-tinged red |
| (139) | —CH₂—CH₂—OC₂H₅ | bluish-tinged red |
| (140) | —CH₂—CH₂—Cl | red |
| (141) | —(CH₂)₃—CH₃ | red |
| (142) | —CH₂—C₆H₄—CH₃(p) | red |
| (143) | —CH₂—CH₂—CN | yellowish-tinged red |
| (144) | —CH₂—CH₂—OCH₂—⌬ | bluish-tinged red |

| Ex. | W | Colour shade (polyester, 100° C.) |
|---|---|---|
| (145) | —CH₂—CH₂Br | red |

EXAMPLE 146

60 g of the compound of the formula (57) in 1,200 ml of ethylene glycol monoethyl ether are heated to the boil for 30 minutes, under reflux and whilst stirring, the mixture is cooled to 105° C., 16 g of potassium carbonate are added, the mixture is heated to 100° C. for 1 hour, 60 g of Na₂S.9H₂O are added and the mixture is stirred for 5 minutes at 110° C. About 160 ml of water-containing solvent are distilled off in the course of 10 minutes, a further 30 g of Na₂S.9H₂O are added, the mixture is stirred at 110° C. for 5 minutes and cooled to room temperature, 250 ml of glacial acetic acid are added dropwise, the crystal suspension is stirred for a further 15 minutes and the crystalline precipitate is filtered off, washed, first with ethanol until the filtrate is clear and then with water, and dried under N₂ at 60° C. in vacuo. 50.4 g of the compound of the formula

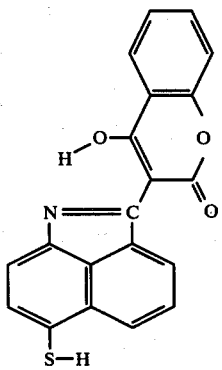

(146)

are obtained.

EXAMPLE 147

34.5 g of the compound of the formula (146) are suspended in 500 ml of methanol, a solution of 2.5 g of sodium in 100 ml of methanol is added, whilst stirring, the mixture is stirred for 10 minutes, 13 g of benzyl chloride are added and the mixture is heated to the boil for 3 hours, under reflux and whilst stirring, and then cooled to 20° C. The crystalline precipitate is filtered off, washed, first with methanol and then with water, and dried in vacuo at 70° C. 39 g of the compound of the formula

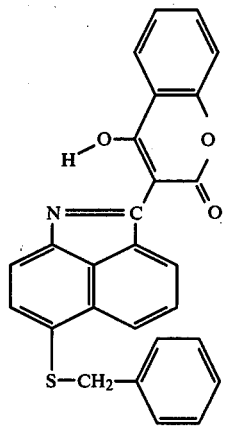

(147)

are obtained. It displays a brilliant red colour shade on polyester.

EXAMPLE 148

15.6 g of the compound of the formula (138) are suspended in 250 ml of glacial acetic acid, 5 g of 30% strength perhydrol are added dropwise at 90° C. whilst stirring, and the mixture is stirred at 95° C. for 5 minutes and cooled. The crystalline precipitate is filtered off, washed with 150 ml of methanol until the filtrate is clear and dried in vacuo at 60° C. 13 g of the compound of the formula

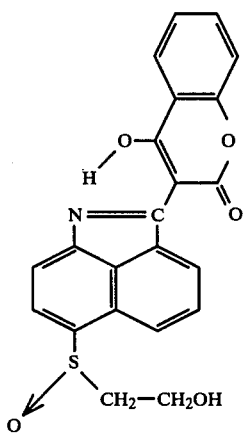

(148)

are obtained in the form of orange coloured crystals. On polyester fibres (130° C., closed vessel), the compound gives a clear, deep reddish-tinged yellow colour shade, which has good fastness properties.

Sulphoxide dyestuffs of similarly good coloristic quality on polyester are obtained when an equivalent amount of compound (106) to (130), (131) to (135), (136), (137), (139) to (145) or (147) is employed in place of compound (138).

EXAMPLE 149

15.6 g of the compound of the formula (138) are suspended in 200 ml of glacial acetic acid and 28 g of 30% strength perhydrol are added dropwise at 90° C., whilst stirring, whereupon a clear solution is transiently formed and a yellow crystalline precipitate then separates out. The mixture is stirred for a further 2 hours at 90° to 95° C. and is then cooled. The crystalline precipitate is filtered off, washed with 150 ml of methanol until the filtrate is clear and dried in vacuo at 60° C. This gives 10 g of the compound of the formula

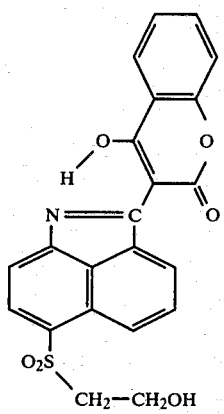
(149)

The dyestuffs of the formula which follows, which are listed in the table which follows, are prepared by the same method. They display valuable colouristic properties similar to those of (149).

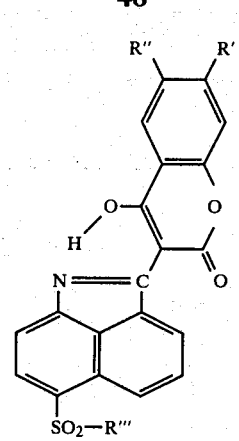

| Example | R''' | R' | R'' | Colour shade on polyester (130° C., high temperature dyeing) |
|---|---|---|---|---|
| (150) | CH₃ | CH₃ | H | brilliant, somewhat reddish-tinged yellow |
| (151) | —(CH₂)₃CH₃ | H | H | brilliant, somewhat reddish-tinged yellow |
| (152) | —(CH₂)₃—CH₂Cl | H | H | brilliant, somewhat reddish-tinged tellow |
| (153) | —CH₂—CH₂—O—C₂H₅ | CH₃O | H | brilliant, dark reddish-tinged yellow |
| (154) | —CH₂—CH₂—CN | H | CH₃ | brilliant, somewhat reddish-tinged yellow |
| (155) | —CH₂—⌬ | H | Cl | brilliant, somewhat reddish-tinged yellow |
| (156) | —CH₂—COOCH₃ | H | H | brilliant, somewhat reddish-tinged yellow |
| (157) | —⌬ | H | H | brilliant, somewhat reddish-tinged yellow |
| (158) | —⌬—CH₃ | H | CH₃ | brilliant, somewhat reddish-tinged yellow |
| (159) | —⌬—Cl | C₂H₅—O | H | brilliant, deep reddish-tinged yellow |
| (160) | —⌬(benzothiazole) | H | H | brilliant, somewhat reddish-tinged yellow |

EXAMPLE 161

11.2 g of the dye salt of Example (60) are finely powdered and suspended in 150 ml of ethylene glycol monoethyl ether, the suspension is stirred for 15 minutes at 40° C., 6 g of potassium carbonate and 2.2 ml of thiophenol are added and the mixture is stirred for 1 hour at 60° C. The reaction mixture is discharged into 500 ml of water and the pH is adjusted to 5 by adding glacial acetic acid. The crystalline precipitate is filtered off, washed with water and dried in vacuo at 50° C. 9.2 g of the compound of the formula and a further 6 g of this compound are obtained from the concentrated mother liquor; the compound is in the form of luminous yellow crystals. on polyester fibres (130° C.), they display a brilliant yellow colour shade which has good fastness properties.

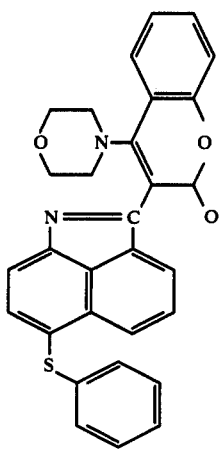

(161)

are obtained as a dark red crystalline powder. When this compound is heated to the boil in 5:1 glacial acetic acid/concentrated hydrochloric acid for 15 minutes and the mixture is then discharged into water, the dyestuff of the formula (106) is obtained.

EXAMPLE 162

100 g of the compound of the formula (106) are introduced into 450 g of chlorosulphonic acid at < 40° C., whilst cooling and stirring, the reaction mixture is stirred for 30 minutes at 120° C. and discharged onto 2.5 kg of ice, whilst stirring, and the mixture is stirred for 5 minutes. The crystalline precipitate is filtered off and dried in vacuo at 25° C. 120 g of the compound of the formula

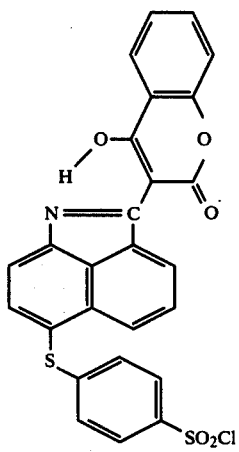

(162)

are obtained as a deep dark red crystalline powder.

EXAMPLE 163

51.9 g of the compound of the formula (162), 12.8 g of piperidine and 86.6 g of sodium carbonate are introduced into a mixture of 670 ml of water and 200 g of ethanol, the reaction mixture is heated to the boil under reflux for 2 hours, whilst stirring, and discharged hot into 4.5 liters of water at 60° C. and the mixture is stirred for 15 minutes. The crystalline precipitate is filtered off, washed with water and dried in vacuo at 70° C. 41 g of the compound of the formula

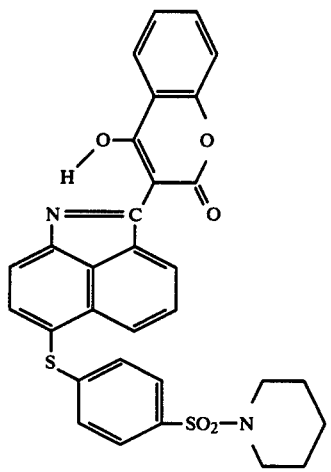

(163)

are obtained as a dark red crystalline powder. When applied to polyester fibres by the high temperature process at 130° C., this compound displays a brilliant red shade which has good fastness properties, such as good fastness to light and sublimation.

The following compounds of the formula

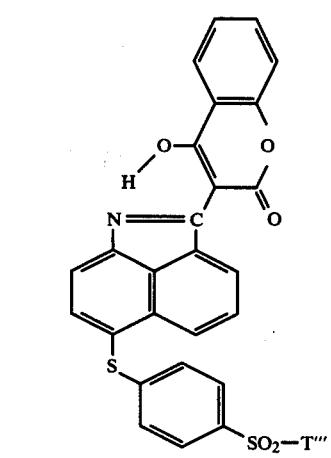

which are coloristically of similar value and are listed in the table, are prepared by the same method.

| Ex. | T''' | Colour shade on polyester (130° C.) |
|---|---|---|
| (164) | —N⟨pyrrolidine⟩ | red |
| (165) | —N⟨morpholine⟩O | red |
| (166) | —N⟨hexamethyleneimine⟩ | red |
| (167) | —N⟨piperazine⟩N—CH₃ | red |

| Ex. | T''' | Colour shade on polyester (130° C.) |
|---|---|---|
| (168) | −N(piperazine)N−CH₂−CH₂OH | red |
| (169) | −NH−CH₂−CH₂−CH₂−N(CH₃)₂ | red |
| (170) | −N((CH₂)₃CH₃)((CH₂)₂CH₃) | red |
| (171) | −N(CH₃)(CH₃) | red |
| (172) | −N(CH₂−CH₂OH)(CH₂−CH₂OH) | red |
| (173) | −N(CH₂−C₆H₅)(CH₂−C₆H₅) | red |
| (174) | −N(CH₂−CH₂Cl)(CH₂−CH₂Cl) | red |
| (175) | −N(CH₂−CH₂−OCH₃)(CH₂−CH₂OCH₃) | red |
| (176) | −NH−C₆H₁₁ (H) | red |
| (177) | −NH−CH₂−C₆H₁₁ (H) | red |
| (178) | −N(piperazine)N−CH₂−CH₂−CH₂−CH₃ | red |

EXAMPLE 179

51.9 g of the compound of the formula (162), 25.7 g of p-chlorophenol and 92.5 g of sodium carbonate are introduced into a mixture of 670 ml of water and 200 g of ethanol, the reaction mixture is heated to the boil under reflux for 16 hours, whilst stirring, and discharged hot into 4.5 liters of water at 60° C. and the mixture is stirred for 15 minutes. The crystalline precipitate is filtered off, washed with water, washed with ethanol and dried in vacuo at 60° C. 59 g of the compound of the formula

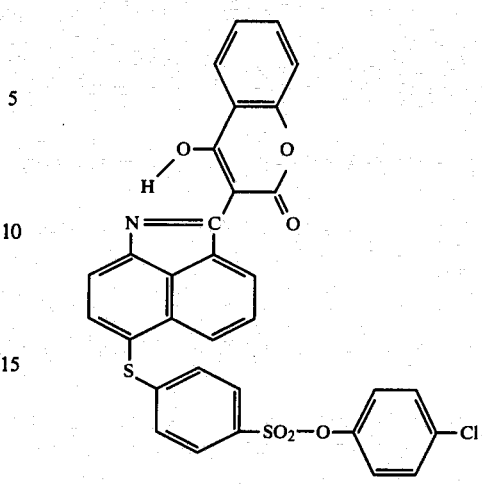

(179)

are obtained as a dark red crystalline powder. This compound dyes polyester fibres (130° C.) in a yellowish-tinged red colour shade which has good fastness properties.

Example (180) which is given in the table is prepared by the same method and the subseqent Examples (181) to (184) which are given in the table are prepared analogously to Example 69: the compounds correspond to the formula

| Example | T''' | Colour shade on polyester (130° C.) |
|---|---|---|
| (180) | −C₆H₄−CH₃ | red |
| (181) | −C₆H₁₁ (H) | red |
| (182) | −CH₂−CH₂−CH(CH₃)₂ | red |
| (183) | −CH₂−C₆H₁₁ (H) | red |
| (184) | −CH(CH₃)−C₆H₅ | red |

EXAMPLE 185

62 g of the compound of the formula (1) and 67 g of boric acid in 2.5 liters of glacial acetic acid and 670 ml of acetic anhydride are heated to the boil under reflux for 7 hours, whilst stirring, and the mixture is cooled to room temperature. The crystalline precipitate is filtered off, washed with a little glacial acetic acid and then with petroleum ether and dried in vacuo at 60° C. 80 g of the compound of the formula

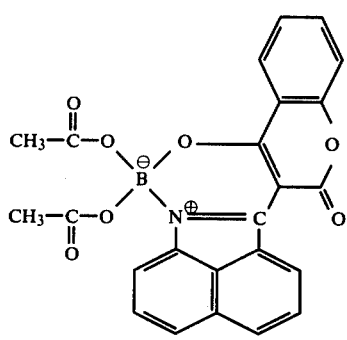

(185)

are obtained in a pure, luminous, orange coloured crystalline form. The compound can be recrystallised without decomposition from dimethylformaide.

On polyester fibres it displays the same properties as the starting compound of the formula (1).

If an equivalent amount of trifluoroacetic anhydride in trifluoroacetic acid, of propionic anhydride in propionic acid or of n-butyric anhydride in butyric acid is employed in place of acetic anhydride, the analogous compounds are obtained. These compounds display similar properties.

The dyestuffs of the formula (2) to (38), (57) to (59), (61), (65) to (68), (83) to (104), or (106) to (160) can also be converted into the corresponding boron compounds by the same method. Compounds such as (138), (148) and (149), which contain an aliphatic OH group, are simultaneously converted into the corresponding o-acyl compounds.

EXAMPLE 186

52 g of the compound of the formula

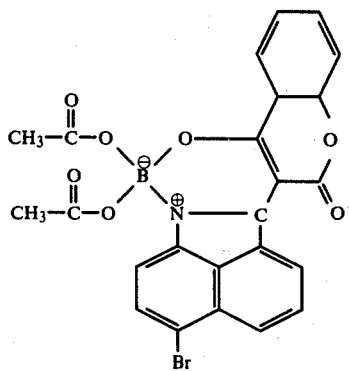

(186)

which is prepared by the method indicated in Example 185, are suspended in 800 ml of ethylene glycol monoethyl ether, 15 g of potassium carbonate and 12 g of thiophenol are added at 40° C. and the mixture is stirred for 20 minutes at 40° C. 30 ml of glacial acetic acid are then added and the mixture is cooled to room temperature. The crystalline precipitate is filtered off, washed with methanol and recrystallised from ethylene glycol monomethyl ether. 46 g of the compound of the formula

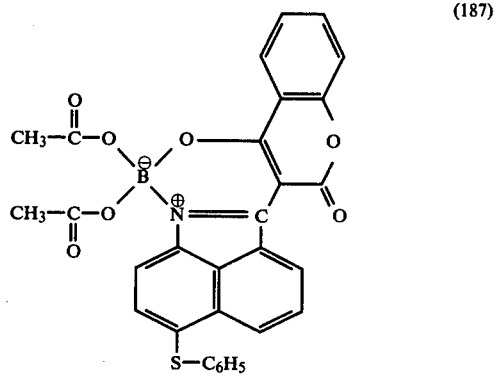

(187)

are obtained as a dark red crystalline powder. On polyester fibres, at 130° C. in a closed dyeing vesel, this compound gives a brilliant, somewhat bluish-tinged colour shade which has good fastness properties, such as good fastness to light and sublimation.

EXAMPLE 188

2 g of boric acid and then 10 g of the compound of the formula (1) are added to a melt of 60 g of benzoic anhydride at 140° C. and the mixture is stirred for 1 hour at 160° C. and cooled to 80° C. 100 ml of methanol are allowed to run in at 80° C. and the solution is cooled to 15° C. The crystalline precipitate is filtered off, washed with petroleum ether and dried in vacuo at 60° C. 17.7 g of the compound of the formula

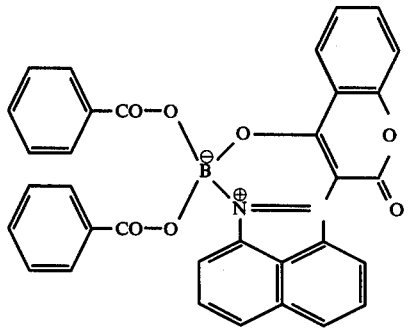

(188)

are obtained as a luminous orange coloured crystalline powder.

In an analogous manner the compound of the formula (189) is prepared as a luminous orange on (57) and the phenylmercapto compound (190) is prepared as a brilliant, bluish-tinged red from (106).

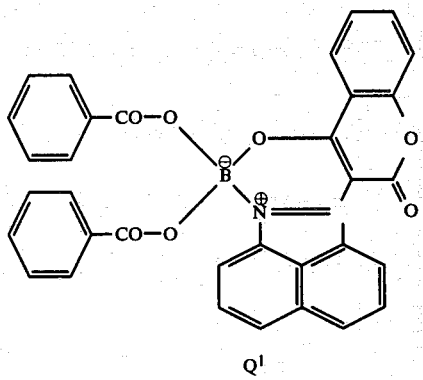

(189) $Q^1$ = Br
(190) $Q^1$ = $C_6H_5$—S—

EXAMPLE 191

15 g of the compound of the formula (188) are introduced, in portions, at 20-25° C. into a mixture of 80 g of 100% strength sulphuric acid and 80 g of oleum (20% of free $SO_3$) and the solution is stirred for 15 hours at 20-25° C. and discharged into 500 ml of water, the temperature being kept at 60° C. by adding ice. 7 g of sodium chloride are added and the mixture is cooled to 20° C. The crystalline precipitate is filtered off, washed with 3% strength sodium chloride solution and dried in vacuo at 40° C. 14 g of the compound of the formula (191)

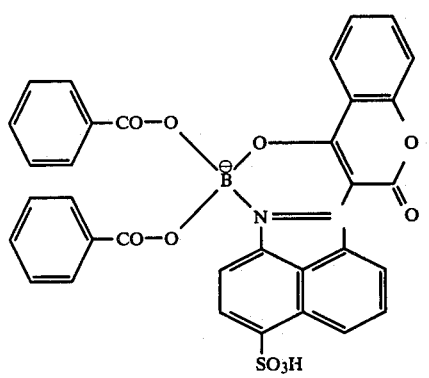

are obtained as an orange coloured crystalline powder. A brilliant reddish-tinged yellow colour shade is obtained on polyamide fibres (Perlon).

We claim:

1. Dyestuff of the formula

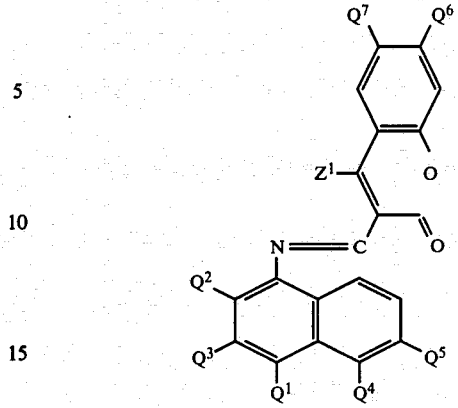

wherein
$Z^1$ represents OH or $NT^1T^2$;
$T^1$ represents H; or $C_1$-$C_4$-alkyl which is unsubstituted or substituted by $C_1$-$C_2$-alkoxy or chlorine;
$T^2$ represents H; or $C_1$-$C_4$-alkyl which is unsubstituted or substituted by $C_1$-$C_2$-alkoxy or chlorine; or conjointly with $T^1$ represents —$(CH_2)_2$-T-$(CH_2)_2$—;
T represents —O—; —NH—; -N($CH_3$)—; —$CH_2$—; or a direct bond;
$Q^1$ represents H; fluorine; chlorine; bromine; iodine; hydroxyl; $C_1$-$C_4$-alkoxy; cyclohexyloxy; benzyloxy; phenoxy; phenylsulphonyloxy; sulphydryl; $C_1$-$C_4$-alkylmercapto unsubstituted or substituted with OH, Cl, Br, CN, $C_1$-$C_2$-alkoxy, benzyloxy or $C_1$—$C_2$-alkoxycarbonyl; benzylmercapto; p-tolylmethylmercapto; phenylmercapto unsubstituted or substituted with $C_1$-$C_4$-alkyl, $C_1$-$C_2$-alkoxy, $CF_3$, chlorine, bromine, amino, C-$C_2$-alkylcarbonylamino, $C_1$—$C_2$-alkylsulphonylamino, chlorosulphonyl, $Q^8O$-SO—, $Q^9Q^{10}N$-$SO_2$- or nitro; naphthylmercapto; amino monosubstituted or disubstituted with $C_1$-$C_4$-alkyl or benzyl or monosubstituted by phenyl; $C_1$-$C_4$-alkylcarbonylaminoor -sulphonylamino unsubstituted or substituted with chlorine; $C_1$-$C_4$-alkylureido; phenylureido; $C_1$-$C_2$-alkoxycarbonylamino; phenoxycarbonylamino; benzoylamino unsubstituted or substituted with methyl, methoxy, or chlorine; nitro; $C_1$-$C_4$-alkylsulphonyl unsubstituted or substituted with chlorine or hydroxyl; phenylsulphonyl or phenylsulphinyl unsubstituted or substituted with $C_1$-$C_4$-alkyl, chlorine, or bromine; chlorosulphonyl; $Q^8O$-$SO_2$—; $Q^9Q^{10}N$-$SO_2$-; $Q^9Q^{10}N$-CO—; $Q^{11}O$-CO—; or cyano;
$Q^2$ represents hydrogen, chlorine bromine, phenylmercapto or ethyl;
$Q^3$ represents hydrogen or bromine;
$Q^4$ represents hydrogen, $C_1$-$C_2$-alkoxy, chlorine, bromine, or phenylmercapto;
$Q^5$ represents hydrogen or bromine;
$Q^6$ represents hydrogen, methyl, hydroxyl, $C_1$-$C_4$-alkoxy, benzyloxy, di-($C_1$-$C_2$-alkyl)-amino, chlorine, or bromine;
$Q^7$ represents hydrogen, methyl, $C_1$-$C_2$-alkoxy, chlorine, or bromine or, conjointly with $Q^6$, represents methylenedioxy or —CH=CH-CH=CH- which is linked to position 5 of the coumarin ring system;

$Q^8$ represents H; $C_4$-$C_8$-alkyl, cyclohexyl unsubstituted or substituted with methyl; or phenyl-$C_1$-$C_3$-alkyl;

$Q^9$ represents unsubstituted $C_1$-$C_6$-alkyl; $C_1$-$C_3$-alkyl which is substituted by OH, Cl, CN, $C_1$-$C_2$-alkoxy, di-($C_1$-$C_2$-alkyl)-amino, morpholino, or tri-($C_1$-$C_2$-alkyl)-ammonium, or phenyl-$C_1$-$C_2$-alkyl, cyclohexyl or cyclohexylmethyl;

$Q^{10}$ represents H; unsubstituted $C_1$-$C_4$-alkyl; or $C_1$-$C_2$-alkyl which is substituted by Oh, Cl, CN or $C_1$-$C_2$-alkoxy; or conjointly with $Q^9$ represents —$(CH_2)_2$-T-$(CH_2)_2$—; and $Q^{11}$ represents H, $C_1$-$C_2$-alkyl, phenyl-$C_1$-$C_2$-alkyl, or phenyl; and wherein either $T^1$ and $T^2$ or $Q^9$ and $Q^{10}$ or both represent —$(CH_2)_2$-T-$(CH_2)_2$—; or an acid salt of the dyestuff with inorganic or organic colorless acids when $Z^1$=$NT^1T^2$.

2. Dyestuff of claim 1, wherein

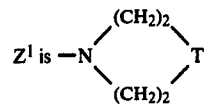

3. Dyestuff of claim 1, wherein

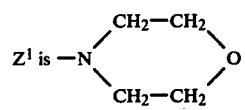

* * * * *